United States Patent
Wang et al.

(10) Patent No.: US 12,097,200 B2
(45) Date of Patent: *Sep. 24, 2024

(54) COMBINATION OF BI853520 WITH CHEMOTHERAPEUTIC DRUGS

(71) Applicant: INXMED (NANJING) CO., LTD., Nanjing (CN)

(72) Inventors: Zaiqi Wang, Shanghai (CN); Jiangwei Zhang, Shanghai (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/347,324

(22) Filed: Jul. 5, 2023

(65) Prior Publication Data

US 2024/0024319 A1    Jan. 25, 2024

Related U.S. Application Data

(63) Continuation of application No. 17/797,867, filed as application No. PCT/CN2021/074371 on Jan. 29, 2021.

(30) Foreign Application Priority Data

Feb. 5, 2020    (CN) .......................... 202010080757.1

(51) Int. Cl.
| | | |
|---|---|---|
| A61K 31/506 | (2006.01) | |
| A61K 9/127 | (2006.01) | |
| A61K 31/337 | (2006.01) | |
| A61K 31/704 | (2006.01) | |
| A61P 35/00 | (2006.01) | |

(52) U.S. Cl.
CPC .......... *A61K 31/506* (2013.01); *A61K 9/1271* (2013.01); *A61K 31/337* (2013.01); *A61K 31/704* (2013.01); *A61P 35/00* (2018.01)

(58) Field of Classification Search
CPC .. A61K 31/337; A61K 31/506; A61K 31/704; A61K 9/1271; A61P 35/00
See application file for complete search history.

(56) References Cited

U.S. PATENT DOCUMENTS

| | | |
|---|---|---|
| 2011/0288071 A1 | 11/2011 | Stadtmueller et al. |
| 2016/0264574 A1 | 9/2016 | Stogniew et al. |
| 2016/0346282 A1 | 12/2016 | Pachter et al. |
| 2018/0177788 A1* | 6/2018 | Pachter .................. A61P 35/00 |
| 2023/0000867 A1 | 1/2023 | Wang et al. |
| 2023/0079055 A1 | 3/2023 | Wang et al. |
| 2023/0145356 A1* | 5/2023 | Wang .................. A61K 31/506 514/235.5 |

FOREIGN PATENT DOCUMENTS

| | | |
|---|---|---|
| CA | 3125058 A1 | 7/2020 |
| CN | 102292322 A | 12/2011 |
| CN | 108289892 A | 7/2018 |
| CN | 111565742 A | 8/2020 |
| EP | 4101453 A1 | 12/2022 |
| WO | 2010058032 A2 | 5/2010 |
| WO | 2012136829 A1 | 10/2012 |
| WO | 2015120289 A1 | 8/2015 |
| WO | 2017004192 A1 | 1/2017 |
| WO | 2020202005 A1 | 10/2020 |
| WO | 2021048339 A1 | 3/2021 |
| WO | 2021104454 A1 | 6/2021 |
| WO | 2021154929 A1 | 8/2021 |
| WO | 2021155764 A1 | 8/2021 |

OTHER PUBLICATIONS

U.S. Appl. No. 18/350,303 filed Jul. 2023, Wang; Zaiqi.*
Laszlo et al. (Journal of Molecular Medicine, 97:231-242, published Dec. 11, 2018). (Year: 2018).*
Solomon et al. (Clinical Lymphoma & Myeloma, vol. 8, No. 1, 21-32, 2008). (Year: 2008).*
Gupta et al. (Molecules, 2018, 23, 1719). (Year: 2018).*
Doi et al., "Phase I Study of the Focal Adhesion Kinase Inhibitor BI 853520 in Japanese and Taiwanese Patients with Advanced or Metastatic Solid Tumors," Targeted Oncology (2019) vol. 14, pp. 57-65.
[No Author Listed] Press Release—"Congratulations! Yingshi BioFAK inhibitor was approved for clinical use in China," retrieved from xueqiu.com/9766314542/137684324, (2019) 3 pages.
International Search Report and Written issued in PCT/CN2021/074371, mailed on Mar. 30, 2021.
[No Author Listed] Press Release: "Yingshi Biotechnology and MSD have reached a global clinical collaboration to evaluate the combination of FAK inhibitors and parolizumab," Medical Mission/Report, Jan. 7, 2020, retrieved from kueqiu.com/9766314542/138813166, three pages, Chinese with English translation.
[No Author Listed] Press Release: "Yingshi Biological FAK Inhibitor IN10018 Phase I Clinical Trial Approved in China," PR Newswire, Dec. 20, 2019, retrieved from prasia.com/story/268783-1.shtml, 2 pages, Chinese with English translation.
[No Author Listed] "Yingshi Announces Clinical Collaboration with Merck & Co., Inc to Evaluate IN10018 Combination with Pembrolizumab," Press Release retrieved from cnmobile.prnasia.com, Oct. 26, 2023, Chinese with English translation.
[No Author Listed] "Congratulations! Instec Fak inhibitors are clinically approved in China," Press release, Medicine Guanlan Report, WuXi AppTec published on Dec. 19, 2019, 3 pages.
[No Author Listed] Machine translation of WO 2021155764 (Year: 2021).
Abuhammad et al, Inhibition of the protein arginine methyltransferase PRMT5 overcomes resistance to CDK4-inhibition in melanoma, Pigment Cell Melanoma Res (2018) vol. 31, p. 125, Abstract from SMR Congress 2017.

(Continued)

*Primary Examiner* — Kara R McMillian
(74) *Attorney, Agent, or Firm* — K&L Gates LLP

(57) ABSTRACT

The present invention relates to a use of BI853520 or a pharmaceutically acceptable salt thereof in preparing drugs for treating tumors in combination with chemotherapeutic drugs.

17 Claims, 5 Drawing Sheets

(56) References Cited

OTHER PUBLICATIONS

Bastin et al., "Salt Selection and Optimization Procedures for Pharmaceutical New Chemical Entities," Organic Process Research & Development (2000) vol. 4, pp. 427-435.
Beierle et al., "TAE226 inhibits human neuroblastoma cell survival," Cancer Investigation (2008) vol. 26, p. 145.151.
Cuiffo et al., "Palmitoylation of oncogenic NRAS is essential for leukemogenesis," Blood (2010) vol. 115, No. 17, pp. 3598-3605.
Dragoj et al., "Targeting CXCR4 and FAK reverses doxorubicin resistance and suppresses invasion in non-small cell lung carcinoma," Cell Oncol (2017) vol. 40, pp. 47-62.
Fredericks et al., "The role of RAS effectors in BCR/ABL induced chronic myelogenous leukemia," Front Med (2013) vol. 7, No. 4, pp. 452-461.
Golubovskaya et al., "Disruption of focal adhesion kinase and p53 interaction with small molecule compound R2 reactivated p53 and blocked tumor growth," BMC Cancer (2013) vol. 13, Article 342, 14 pages.
Golubovskaya et al., "MIR-138 and MiR-135 Directly Target Focal Adhesion Kinase, Inhibit Cell Invasion, and Increase Sensitivity to Chemotherapy in Cancer Cells," Anticancer Agents Med Chem (2014) vol. 14, No. 1, pp. 18-28.
He et al., "Studies on the Role of Focal Adhesion Kinase in Disease," Acta Neuropharmacologica (2021) vol. 11, No. 3, pp. 50-64. Chinese with English abstract.
Hirata et al., "Intravital Imaging Reveals How BRAF Inhibition Generates Drug-Tolerant Microenvironments with High Integrin Beta1/FAK Signaling," Cancer Cell (2015) vol. 27, pp. 574-588.
Hirt et al., "Efficacy of the highly selective focal adhesion kinase inhibitor BI 853520 in adenocarcinoma xenograft models is linked to a mesenchymal tumor phenotype," Oncogenesis (2018) vol. 7, Article 21, 11 pages.
Kurenova et al., "A Fak scaffold inhibitor disrupts FAK and VEGFR-3 signaling and blocks melanoma growth by targeting both tumor and endothelial cells," Cell Cycle (2014) vol. 13, Iss. 16, pp. 2542-2533.
Kurenova et al., "The Small Molecule Chloropyramine Hydrochloride (C4) Targets the Binding Site of Focal Adhesion Kinase and Vascular Endothelial Growth Factor Receptor 3 and Suppresses Breast Cancer Growth in vivo," J Med Chem (2009) vol. 52, No. 15, pp. 4716-4724.
Lee et al., "FAK signaling in human cancer as a target for therapeutics," Pharmacology & Therapeutics (2015) vol. 146, pp. 132-149.
Li et al., "The impact of Pegylated liposomal doxorubicin in recurrent ovarian cancer: an updated meta-analysis of randomized clinical trials," Journal of Ovarian Research (2021) vol. 14, Article 42, 12 pages.
Mohanty et al., "FAK-targeted and combination therapies for the treatment of cancer: an overview of phase I and II clinical trials," Expert Opinion on Investigational Drugs (2020) vol. 29, No. 4, pp. 399-409.
Parikh et al., "Oncogenic NRAS, KRAS, and HRAS Exhibit Different Leukemogenic Potentials in Mice," Cancer Res (2007) vol. 67, No. 15, pp. 7139-7146.
Signorelli et al., "Cobimetinib: A Novel MEK Inhibitor for Metastatic Melanoma," Annals of Pharmacotherapy (2017) vol. 51, No. 2, pp. 146-153.
Tavora et al., "Endothelial-cell FAK targeting sensitizes tunours to DNA-damaging therapy," Nature (2014) vol. 514, pp. 112-116 and Methods pages.
Tiede et al., "The FAK inhibitor BI 853520 exerts anti-tumor effects in breast cancer," Oncogenesis (2018) vol. 7, Article 73, 19 pages.
Yu et al., "Connexin 32 affects doxorubicin resistance in hepatocellular carcinoma cells mediated by Src/FAK signaling pathway," Biomedicine & Pharmacotherapy (2017) vol. 95, pp. 1844-1852.
Zhang et al., "A Simple Statistical Parameter for Use in Evaluation and Validation of High Throughput Screening Assays," Journal of Biomolecular Screening (1999) vol. 4, No. 2, pp. 67-73.
Zhang et al., "Bcr-Abl Efficiently Induces a Myeloproliferative Disease and Production of Excess Interleukin-3 and Granulocyte-Macrophase Colony-Stimulating Factor in Mice: A Novel Model for Chronic Myelogenous Leukemia," Blood (1998) vol. 92, No. 10, pp. 3829-3840.
Zhang et al., "Efficacy of focal adhesion kinase inhibition in non-small cell lung cancer with oncogenically activated MAPK pathways," British Journal of Cancer (2016) vol. 115, pp. 203-211.
Zhang et al., "Gain-of-Function RHOA Mutatations Promote Focal Adhesion Kinase Activation and Dependency in Diffuse Gastric Cancer," Cancer Discovery (2020) vol. 10, pp. 288-305.
Zhang et al., "Focal Adhesion Kinase (FAK) Inhibition Synergizes with Kras G12C Inhibitors in Treating Cancer through the Regulation of the FAK-YAP Signaling," Advanced Science (2021) vol. 8, Article e2100250, 15 pages.

* cited by examiner

COMBINATION OF BI853520 WITH CHEMOTHERAPEUTIC DRUGS

CROSS-REFERENCE TO RELATED APPLICATIONS

This application is a continuation of U.S. application Ser. No. 17/797,867, filed Aug. 5, 2022. U.S. application Ser. No. 17/797,867 is a U.S. National Phase Application under 35 U.S.C. § 371 of International Application No. PCT/CN2021/074371, filed Jan. 29, 2021, which claims the priority of Chinese Patent Application No. 202010080757.1 filed on Feb. 5, 2020. The contents of all of these applications are incorporated herein by reference as a part of this application.

FIELD OF THE INVENTION

The present disclosure belongs to the field of pharmaceutical chemistry. Particularly, the present disclosure relates to use of BI853520 or a pharmaceutically acceptable salt thereof in the manufacture of a medicament for treating tumors in combination with a chemotherapeutic drug.

BACKGROUND OF THE INVENTION

Cancer is one of the most serious diseases that threaten human life and health. Seven million people die from cancer worldwide every year. At present, there are four main methods of cancer treatment: surgery, drug therapy, radiation therapy and immunotherapy, in addition to adjuvant therapy. Among them, the drug therapy of cancer includes targeted drug therapy and chemotherapy. Among the current treatment methods, targeted drug therapy and chemotherapy still occupy an important position and are important standard therapies for cancer. For example, the combined chemotherapy of carboplatin/paclitaxel is the first-line treatment regimen for ovarian cancer, and chemotherapeutic drugs such as paclitaxel are also indispensable in the treatment regimen for gastric cancer. However, the biggest problem of targeted drug therapy and chemotherapeutic drug monotherapy is drug resistance, including spontaneous drug resistance and adaptive drug resistance, which results in a low overall remission rate and a limited duration of remission.

Therefore, finding a way to improve the efficacy of a single drug in chemotherapy and further overcome the problem of drug resistance is a technical problem that urgently needs to be solved in cancer treatment.

SUMMARY OF THE INVENTION

In one aspect, the present disclosure provides use of BI853520 or a pharmaceutically acceptable salt thereof in the manufacture of a medicament for treating tumors in combination with a chemotherapeutic drug, wherein the BI853520 is 2-fluoro-5-methoxy-4-[(4-(2-methyl-3-oxo-2,3-dihydro-1H-isoindole-4-oxy)-5-trifluoromethyl-pyrimidin-2-yl)amino]-N-(1-methyl-piperidin-4-yl)benzamide (see WO2010058032) and has a structure of:

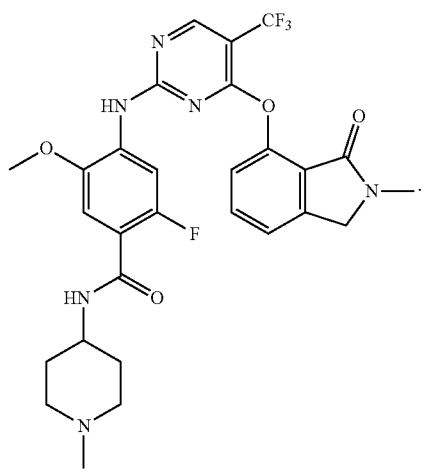

Optionally, the chemotherapeutic drug is PLD, taxane or cisplatin.

Optionally, the tumor does not include an NRAS-mutated tumor.

Optionally, the tumor is acute lymphocytic leukemia, acute myelocytic leukemia, malignant lymphoma, breast cancer, lung cancer, ovarian cancer, soft tissue sarcoma, osteosarcoma, rhabdomyosarcoma, Ewing's sarcoma, blastoma, neuroblastoma, bladder cancer, thyroid cancer, prostate cancer, head and neck squamous cell carcinoma, nasopharyngeal cancer, esophageal cancer, testicular cancer, gastric cancer, liver cancer, pancreatic cancer or melanoma.

Optionally, the tumor is prostate cancer, esophageal cancer, ovarian cancer, gastric cancer or lung cancer. The lung cancer is preferably squamous cell lung cancer.

Optionally, the chemotherapeutic drug is PLD.

Optionally, the tumor is ovarian cancer, especially platinum-resistant ovarian cancer.

Optionally, the chemotherapeutic drug is taxane, especially docetaxel or paclitaxel.

Optionally, the tumor is prostate cancer, esophageal cancer or gastric cancer.

Optionally, the pharmaceutically acceptable salt is BI853520 tartrate.

In another aspect, the present disclosure provides use of BI853520 or a pharmaceutically acceptable salt thereof and a chemotherapeutic drug in the manufacture of a medicament for treating tumors, wherein the BI853520 has a structural formula of:

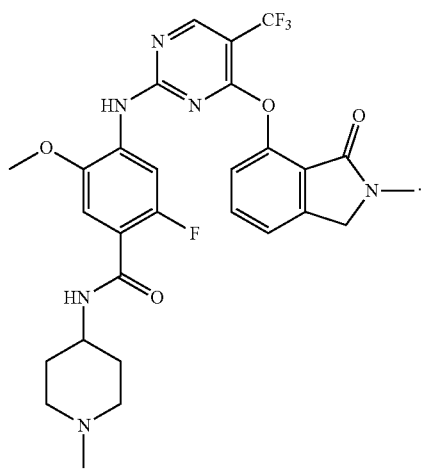

Optionally, the chemotherapeutic drug is PLD, taxane or cisplatin.

Optionally, the tumor does not include an NRAS-mutated tumor.

Optionally, the tumor is acute lymphocytic leukemia, acute myelocytic leukemia, malignant lymphoma, breast cancer, lung cancer, ovarian cancer, soft tissue sarcoma, osteosarcoma, rhabdomyosarcoma, Ewing's sarcoma, blastoma, neuroblastoma, bladder cancer, thyroid cancer, prostate cancer, head and neck squamous cell carcinoma, nasopharyngeal cancer, esophageal cancer, testicular cancer, gastric cancer, liver cancer, pancreatic cancer or melanoma.

Optionally, the tumor is prostate cancer, esophageal cancer, ovarian cancer, gastric cancer or lung cancer. The lung cancer is preferably squamous cell lung cancer.

Optionally, the chemotherapeutic drug is PLD.

Optionally, the tumor is ovarian cancer, especially platinum-resistant ovarian cancer.

Optionally, the chemotherapeutic drug is taxane, especially docetaxel or paclitaxel.

Optionally, the tumor is prostate cancer, esophageal cancer or gastric cancer.

Optionally, the pharmaceutically acceptable salt is BI853520 tartrate.

In another aspect, the present disclosure provides a pharmaceutical combination including BI853520 or a pharmaceutically acceptable salt thereof, and a chemotherapeutic drug; wherein the BI853520 has a structural formula of:

Optionally, the chemotherapeutic drug is PLD, taxane or cisplatin.

Optionally, the chemotherapeutic drug is PLD.

Optionally, the chemotherapeutic drug is taxane, especially docetaxel or paclitaxel.

Optionally, the pharmaceutically acceptable salt is BI853520 tartrate.

In another aspect, the present disclosure provides a method for treating tumors, which comprises administering to a subject BI853520 or a pharmaceutically acceptable salt thereof and a chemotherapeutic drug; wherein the BI853520 has a structural formula of:

Optionally, the method comprises administering to the subject the BI853520 or a pharmaceutically acceptable salt thereof and an effective amount of the chemotherapeutic drug.

Optionally, the chemotherapeutic drug is PLD, taxane or cisplatin.

Optionally, especially an effective amount of BI853520 and an effective amount of PLD, taxane or cisplatin are administered.

Optionally, the tumor does not include an NRAS-mutated tumor.

Optionally, the tumor is acute lymphocytic leukemia, acute myelocytic leukemia, malignant lymphoma, breast cancer, lung cancer, ovarian cancer, soft tissue sarcoma, osteosarcoma, rhabdomyosarcoma, Ewing's sarcoma, blastoma, neuroblastoma, bladder cancer, thyroid cancer, prostate cancer, head and neck squamous cell carcinoma, nasopharyngeal cancer, esophageal cancer, testicular cancer, gastric cancer, liver cancer, pancreatic cancer or melanoma.

Optionally, the tumor is prostate cancer, esophageal cancer, ovarian cancer, gastric cancer or lung cancer. The lung cancer is preferably squamous cell lung cancer.

Optionally, the chemotherapeutic drug is PLD.

Optionally, the tumor is ovarian cancer, especially platinum-resistant ovarian cancer.

Optionally, the chemotherapeutic drug is taxane, especially docetaxel or paclitaxel.

Optionally, the tumor is prostate cancer, esophageal cancer or gastric cancer.

Optionally, the BI853520 or a pharmaceutically acceptable salt thereof and the chemotherapeutic drug are administered simultaneously, alternately or sequentially.

Optionally, it is characterized in that the pharmaceutically acceptable salt is BI853520 tartrate.

DETAILED DESCRIPTION OF THE INVENTION

Figure 1A:
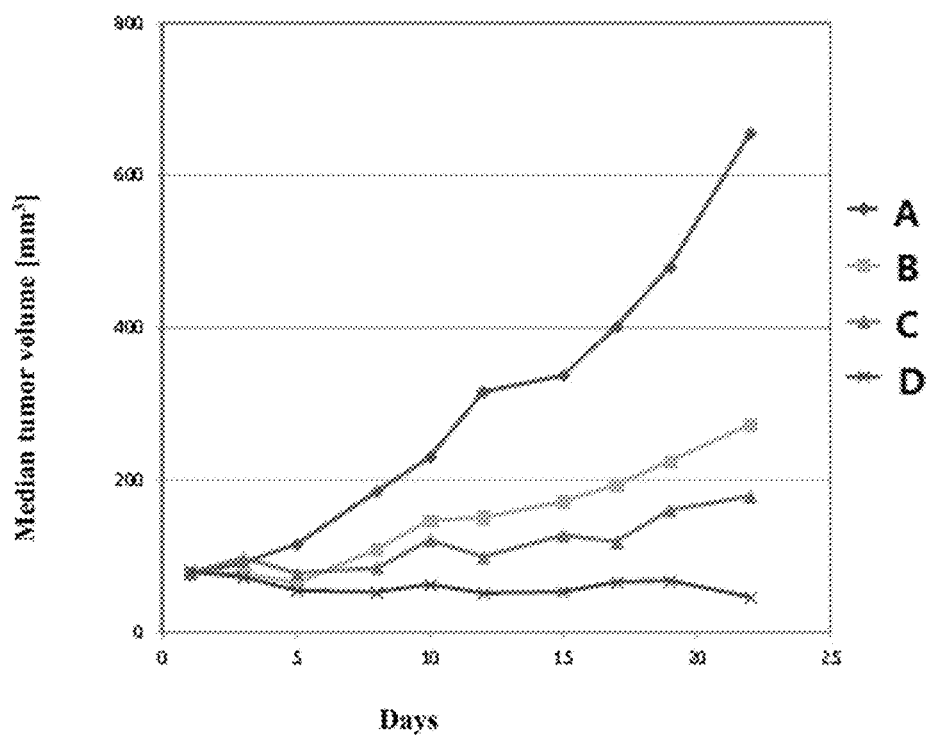
FIG. 1a depicts the median tumor volume in a mouse model of human ovarian cancer (TOV-21G cell line) with BI 853520 and PLD alone or in combination, showing the antitumor activity of different test groups. The test groups were group A (the control group); group B (the BI 853520 group administered once a day at a dose of 12.5 mg/kg); group C (the PLD group administered once a week at a dose of 1 mg/kg); and Group D (the combination group of BI 853520 and PLD, wherein BI 853520 was administered once a day at a dose of 12.5 mg/kg, and PLD was administered once a week at a dose of 1 mg/kg); respectively.

The following examples are provided to further illustrate the present disclosure. It should be understood that these examples are only used to illustrate the present disclosure and not to limit the scope of the present disclosure.

The experimental methods without specific conditions in the following examples can be carried out according to the conventional conditions of this type of reaction or according to the conditions suggested by the manufacturers The experimental materials and reagents used in the following examples can be obtained from commercial sources unless otherwise specified.

The present disclosure relates to the use of BI853520 or a pharmaceutically acceptable salt thereof in the manufacture of a medicament for treating tumors in combination with a chemotherapeutic drug. The present disclosure also relates to the use of BI853520 or a pharmaceutically acceptable salt thereof and a chemotherapeutic drug in the manufacture of a medicament for treating tumors. The present disclosure also relates to a method for treating tumors, which comprises administering to a subject an effective amount of BI853520 or a pharmaceutically acceptable salt thereof and a chemotherapeutic drug.

The term "chemotherapy" as used herein refers to a systemic treatment of malignant tumors, which distributes a chemotherapeutic drug into most organs and tissues throughout the body via blood circulation after the chemotherapeutic drug is administered orally, intravenously, or through body cavity. Chemotherapeutic drugs may function at different phases of tumor cell growth and reproduction, inhibiting or killing tumor cells. It is one of the most effective methods for treating malignant tumors. In some embodiments, the chemotherapeutic drug is PLD, docetaxel, paclitaxel, or cisplatin.

In some embodiments, the tumor does not include an NRAS-mutated tumor. In some embodiments, the tumor is selected from acute lymphocytic leukemia, acute myelocytic leukemia, malignant lymphoma, breast cancer, undifferentiated small cell bronchopulmonary carcinoma, non-small cell bronchopulmonary carcinoma, non-small cell lung cancer, squamous cell lung cancer, ovarian cancer, soft tissue sarcoma, osteosarcoma, rhabdomyosarcoma, Ewing's sarcoma, blastoma, neuroblastoma, bladder cancer, thyroid cancer, prostate cancer, head and neck squamous cell carcinoma, nasopharyngeal cancer, esophageal cancer, testicular cancer, gastric cancer, liver cancer, pancreatic cancer and melanoma. In some embodiments, the tumor is ovarian cancer, gastric cancer, or squamous cell lung cancer.

In another embodiment of the present disclosure, the chemotherapeutic drug is PLD.

The term "PLD" as used herein refers to pegylated liposomal doxorubicin, also known as doxorubicin liposome.

The terms "combination", "combination therapy" and "combination administration" as used herein refer to using two or more drugs for the treatment of one disease. In some embodiments, the BI853520 or a pharmaceutically acceptable salt thereof is used in combination with a chemotherapeutic drug, which may further include other drug(s). In some embodiments, the BI853520 or a pharmaceutically acceptable salt thereof and the chemotherapeutic drug may be administered simultaneously, alternately or sequentially.

The term "NRAS" as used herein refers to an oncogene that is a member of the RAS oncogene family which also includes two other genes: KRAS and HRAS. These genes play important roles in cell division, cell differentiation and apoptosis.

The term "NRAS mutation" as used herein means that when a pathogenic mutation occurs in the NRAS gene, the N-Ras protein encoded by it will be in a state of continuous activation, resulting in uncontrolled cell proliferation and tumor formation.

As used herein, the term "pharmaceutically acceptable" means non-toxic, biologically tolerable and suitable for administration to a subject.

As used herein, the term "pharmaceutically acceptable salt" refers to a salt that is non-toxic, biologically tolerable and suitable for administration to a subject. The pharmaceutically acceptable salts of the compounds refer to an acid addition salt that is non-toxic, biologically tolerable and suitable for administration to a subject, including but not limited to: acid addition salts formed by the compounds with an inorganic acid, such as hydrochloride, hydrobromide, carbonate, bicarbonate, phosphate, sulfate, sulfite, nitrate, and the like, as well as acid addition salts formed by the compounds with an organic acid, such as formate, acetate, malate, maleate, fumarate, tartrate, succinate, citrate, lactate, methanesulfonate, p-toluenesulfonate, 2-hydroxyethanesulfonate, benzoate, salicylate, stearate, and salts formed with alkane-dicarboxylic acid of formula HOOC—$(CH_2)_n$—COOH (wherein n is 0-4), etc. Pharmaceutically acceptable salts can be obtained by conventional methods well known in the art, for example by reacting a sufficiently basic compound such as an amine with a suitable acid which provides a physiologically acceptable anion. In some embodiments, the salt is a tartrate salt.

As used herein, the term "subject" refers to mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

The term "treat", "treating" or "treatment" as used herein refers to obtaining a desired pharmacological and/or physiological effect. The effect may be therapeutic and includes partial or substantial achievement of one or more of the following: partial or total reduction in the extent of the disease, condition or syndrome; improvement in clinical symptoms or indicators associated with the disease; or delaying, inhibiting or reducing likelihood of progression of the disease, condition or syndrome.

The term "effective amount" as used herein refers to an amount of the BI853520 (or a pharmaceutically acceptable salt thereof), or the chemotherapeutic drug (especially PLD, docetaxel or cisplatin) sufficient to reduce or ameliorate the severity, duration, progression, or onset of the disease or condition, to delay or arrest the progression of the disease or condition, to cause regression of the disease or condition or delay the recurrence or progression of symptoms, or to enhance or improve the therapeutic effect of another therapy. The precise amount of the BI853520 (or a pharmaceutically acceptable salt thereof) and the chemotherapeutic drug (especially PLD, docetaxel or cisplatin) administered to a subject will depend on various factors, such as the given agent or compound, pharmaceutic preparation, route of administration, the type of disease, the condition, the identity of the subject or host being treated, etc., but can still be routinely determined by those skilled in the art. For example, determination of an effective amount will also depend on the degree, severity, and type of cell proliferation. The skilled artisan will be able to determine the appropriate dosage based on these and other factors. When co-administered with other therapeutic agents, e.g., when co-administered with an anticancer agent, the "effective amount" of any other therapeutic agent will depend on the type of the agent used. Appropriate dosages are known for approved therapeutics and can be adjusted by the skilled artisan depending on the condition of the subject, the type of condition being treated, and the amount of the compound or a pharmaceutically acceptable salt thereof. In cases where the amount is not explicitly stated, the amount should be assumed to be an effective amount. An effective dose of the BI853520 (or a pharmaceutically acceptable salt thereof) may range from 10 μg to 2000 mg. This example is non-limiting. Effective amounts of the chemotherapeutic drug (especially PLD, docetaxel or cisplatin) are known to those skilled in the art.

The BI853520 (or pharmaceutically acceptable salts thereof) can be administered by any suitable method of administration. Suitable methods include oral, intravenous, intramuscular or subcutaneous administration to the subject.

Thus, the BI853520 (or a pharmaceutically acceptable salt thereof) can be administered orally with a pharmaceutically acceptable carrier such as an inert diluent or an absorbable edible carrier. They can be enclosed in hard- or soft-shell gelatin capsules, compressed into tablets, or mixed directly with the patient's food. For oral therapeutic administration, the compound, or a pharmaceutically acceptable salt thereof, can be in combination with one or more excipients and used in a form of ingestible tablets, buccal tablets, lozenges, capsules, elixirs, suspensions, syrups or wafers. These preparations contain an effective amount of the BI853520 (or a pharmaceutically acceptable salt thereof).

Tablets, lozenges, pills, capsules, etc. may further comprise: binders such as tragacanth, acacia, cornstarch or gelatin; excipients such as dicalcium phosphate; disintegrants such as corn starch, potato starch, alginic acid, etc.; lubricants, such as magnesium stearate; or sweeteners, such as sucrose, fructose, lactose or aspartame; or flavoring agents.

The BI853520 (or a pharmaceutically acceptable salt thereof) may also be administered intravenously or intraperitoneally by infusion or injection. Solutions of the BI853520 (or a pharmaceutically acceptable salt thereof) and the chemotherapeutic drug (especially PLD, docetaxel or cisplatin) can be prepared in water, optionally mixed with a nontoxic surfactant.

Exemplary pharmaceutical dosage forms for injection or infusion include: sterile aqueous solutions, dispersions, or sterile powders containing the active ingredient suitable for the extemporaneous preparation of sterile injectable or infusion solutions or dispersions. In any event, the final dosage form should be sterile, fluid, and stable under the conditions of manufacture and storage.

Sterile injectable solutions can be prepared by incorporating a required amount of the BI853520 (or a pharmaceutically acceptable salt thereof) in an appropriate solvent together with other desired ingredients enumerated above and then being filtrated and sterilized. In the case of sterile powders for preparing sterile injectable solutions, the preferred methods of preparation may be vacuum drying and the freeze-drying techniques, which yield a powder of the active ingredient plus any other desired ingredients previously present after sterile filtration.

The amount of the BI853520 (or a pharmaceutically acceptable salt thereof), or the chemotherapeutic drug (especially PLD, docetaxel or cisplatin) may vary not only with the particular salt chosen, but also with the route of administration, the nature of the disease being treated, and the age and condition of the patient, and is ultimately at the discretion of the attending physician or clinician. However, the dosage may generally range from about 0.1 to about 50 mg/kg body weight per day.

The desired dose may conveniently be presented as a single dose or as divided doses for administration at appropriate intervals.

The meanings of the abbreviations used herein are as follows:
ATCC American Type Culture Collection
ATVs Absolute tumor volume
BID Administered twice daily
BWL Body weight loss
CV Coefficient of variation
$CO_2$ Carbon dioxide
CR Complete response
d Days
ECACC European Collection of Authenticated Cell Cultures
EDTA Ethylene diamine tetraacetic acid
FCS Fetal Calf Serum
H Hours
kg Kilograms
IV Intravenous administration
IP Intraperitoneal administration
0.5% Natrosol 0.5% Hydroxyethyl Cellulose
mg Milligram
ml Milliliter
$mm^3$ Cubic millimeter
MCB Master Cell Bank
Mean Average value
MTD Maximum tolerated dose
MTV Mean tumor volume
N/n Sample number
PBS Phosphate Buffered Saline
PDX Patient-derived xenograft model
PLD Pegylated liposomal doxorubicin
RPMI 1640 RPMI 1640 Medium
p.o. By mouth
PR Partial response
qd/QD per day
SEM Standard error of the mean
TFS Tumor-free survivors
TGI Tumor Growth Inhibition
TV Tumor Volume
WCB Working Cell Bank Antitumor Research Methods in Generic Xenograft Models:

Athymic female BomTac: NMRI-Foxn1nu mice were purchased from Taconic, Denmark. After arriving in the animal room, mice were acclimated to the new environment for at least 3 days before being used for assay. The animals were housed under standard conditions (temperature 21.5±1.5° C. and 55±10% humidity), and provided with standard diet and autoclaved tap water ad libitum. A transponder Datamars T-IS 8010 FDX-B implanted subcutaneously in the neck region and a LabMax II fixed reader were used to identify each mouse. The cage card showed study number, animal identification number, compound and dose level, route of administration, and dosing schedule for animals throughout the assay.

To establish subcutaneous tumors, human cancer cells were harvested by trypsinization, centrifuged, washed and suspended in a suitable medium. 100 μl of the cell suspension containing $5\times10^6$-$1\times10^7$ cells were then injected subcutaneously into the right flank of nude mice (1 site per mouse). When tumors grew to an appropriate size, mice were randomly assigned to a treatment group or a control group.

BI853520 was synthesized according to the method in patent WO2010058032. The dry powder was suspended in an equimolar volume of 1 M HCl and diluted in an appropriate volume of 0.5% Natrosol to achieve the desired concentration for each assay.

Tumor diameters were measured with calipers three times a week (Monday, Wednesday, and Friday). The volume of each tumor [in $mm^3$] was calculated according to the equation, "tumor volume=length×$diameter^2$×π/6". To monitor the side effects of the treatment, the mice were checked daily for abnormalities and their body weights were measured three times a week (Monday, Wednesday, and Friday). Animals were sacrificed at the end of the study (approximately three weeks after the start of treatment). During the study animals with tumor necrosis or tumors larger than 2000 $mm^3$ were sacrificed ahead of schedule for ethical reasons.

At the end of the assay, statistical evaluation of tumor volume and body weight parameters was performed. Absolute tumor volume and percent change in body weight (referenced to initial weight on day 1) were used. A non-parametric approach was used, and the number of observations, median, minimum and maximum values were calculated. For a quick overview of possible treatment effects, the median tumor volume for each treatment group T and the median tumor volume for the control group C were used to calculate the TGI from day 1 to day d:

At the end of the assay, statistical evaluation of tumor volume and body weight parameters was performed. For tumor volume, absolute values were used. A nonparametric approach was used, and the number of observations, median, minimum and maximum values were calculated. For a quick overview of possible treatment effects, the median tumor volume for each treatment group T and the median tumor volume for the control group C were used to calculate the TGI from day 1 to day d:

TGI from day 1 to day d:

$$TGI = 100 * \frac{(C_d - C_1) - (T_d - T_1)}{(C_d - C_1)}$$

wherein, $C_1$, $T_1$=median tumor volume in control and treatment groups at the start of the assay (day 1)

$C_d$, $T_d$=median tumor volume in control and treatment groups at the end of the assay (day d)

Appropriate statistical methods were used for evaluation. Significance level was fixed at α=5%. A p-value (adjusted) of less than 0.05 was considered to show a statistically significant difference between groups, and 0.05≤p-value<0.10 was considered as an indicative difference.

Example 1: Antitumor Activity Study of BI 853520 in Combination with PLD in a Mouse Model of Human Ovarian Cancer Antitumor Research Methods in Generic Xenograft Models were adopted. Mice were approximately 6 weeks old. Each group had 7-10 mice.

TOV-21G cells harboring KRAS and PIK3CA gene mutations were obtained from ATCC (CRL-11730). MCB and WCB were established according to BI RCV GmbH & Co KG standard. Cells were incubated in a T175 tissue culture flask in a medium: RPMI-1640 supplemented with L-glutamine, sodium pyruvate, non-essential amino acids and 10% heat-inactivated fetal bovine serum. Cells were incubated at 37° C. and 5% $CO_2$.

A2780 cells harboring PTEN gene mutations were obtained from ECACC (93112519). MCB and WCB were established according to BI RCV GmbH & Co KG standard. Cells were incubated in a T175 tissue culture flask in a medium: RPMI-1640+Glutamax supplemented with 10% heat-inactivated fetal bovine serum. Cells were incubated at 37° C. and 5% $CO_2$.

SKOV-3 cells harboring CDKN2, MLH1, PIK3CA and TP53 gene mutations were obtained from ATCC (HTB-77). MCB and WCB were established according to BI RCV GmbH & Co KG standard. Cells were incubated in a T175 tissue culture flask in a medium: IMDM+L-Glutamax and non-essential amino acids supplemented with 10% heat-inactivated fetal bovine serum. Cells were incubated at 37° C. and 5% $CO_2$.

A2780 cells were suspended in ice-cold PBS+5% FCS and growth factor-reduced Matrigel (1:1) at a cell inoculation level of 5×10⁶ cells/ml. The TOV-21G cells were suspended in ice-cold PBS+5% FCS at a cell inoculation level of 5×10⁶ cells/ml. When tumors were established and reached 5-8 mm in diameter, mice were randomly assigned to treatment and control groups.

The pH of the BI853520 formulation was between 3 and 4.

PLD (Doxil) was purchased from Johnson & Johnson and dissolved in sterile 5% glucose solution.

Treatment was initiated when the median tumor volume was between 70 and 110 $mm^3$.

TOV-21G:

There were 10 animals in the control group and 7 animals in each treatment group.
A: Control group: 0.5% Natrosol
B: BI 853520: 12.5 mg/kg (once a day, administered by gavage needle)
C: PLD: 1 mg/kg (once a week, administered by intravenous bolus)
D: Combination of B+C

SKOV-3:

There were 10 animals in the control group and 7 animals in each treatment group.
A: Control group: 0.5% Natrosol
B: BI 853520: 50 mg/kg (once a day, administered by gavage needle)
C: PLD: 5 mg/kg (once a week, administered by intravenous bolus)
D: Combination of B+C

A2780:

There were 10 animals in each of the control group and the treatment groups.
A: Control group: 0.5% Natrosol
B: BI 853520: 12.5 mg/kg (once a day, administered by gavage needle)
C: BI 853520: 25 mg/kg (once a day, administered by gavage needle)
D: BI 853520: 50 mg/kg (once a day, administered by gavage needle)
E: PLD: 5 mg/kg (once a week, administered by intravenous bolus)
F: Combination of D+E The three tests used the same method but were evaluated separately. Tumor volume and body weight parameters were statistically evaluated at the end of the test (day 15 or 22).

In cell line A2780, values for animals 2, 6, 7 and 8 (reference values: 0.5% Natrosol; 0.9% NaCl), animals 12 and 17 (12.5 mg/kg BI 853520) and animal 36 (50 mg/kg BI 853520), were sacrificed for ethical reasons since their tumor had reached a critical volume.

Each dose of test compound was compared to the control group using a one-sided descending wilcoxon test, taking reduction in tumor volume as a treatment effect and weight loss as a side effect. The P-values for tumor volume (the efficacy parameter) were compared and adjusted for multiple times according to Bonferroni-Holm, while the P-values for body weight (the tolerance parameter) were not adjusted so as not to overlook possible side effects.

TOV-21G:

Animals in group A had lost 1.5% body weight (FIG. 3a; Table 5), and their tumors had reached a median volume of 654 $mm^3$ on day 22 of treatment (FIG. 1a; Table 1).

There was no tumor regression in group B with a TGI of 67% (p=0.0023) (FIG. 1a; Table 1). Animal body weight increased by 3.1% (p=0.9977 vs. group A) (Table 2).

Group C had a TGI of 83% (p=0.002) with no tumor regression (FIG. 1a; Table 1). Animal body weight increased by 1.6% (p=0.9649 vs. group A) (Table 2).

Group D had a TGI of 106% (p=0.0002 vs. group A; p=0.0006 vs. group B; p=0.0006 vs. group C), and tumor regression occurred in 6 of 7 animals (FIG. 1a; Table 1). Animal body weight increased by 1.4% (p=0.9335 vs. group A; p=0.1914 vs. group B; p=0.5000 vs. group C) (Table 2).

Studies have shown that the TOV-21G cell line was very sensitive to both BI 853520 and PLD. Therefore, both drugs as a single drug showed good efficacy at low doses (12.5 mg/kg; 1 mg/kg), but tumor regression was not induced. In contrast, the combination of the two drugs resulted in tumor regression in 6 of 7 animals and was well tolerated.

Figure 1B:
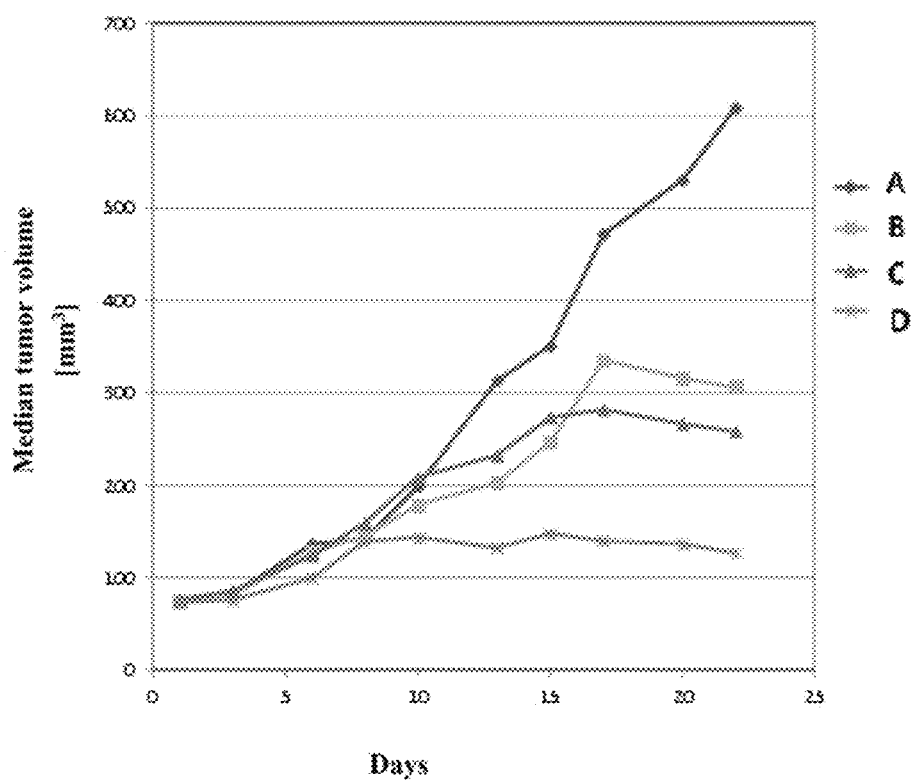
FIG. 1b depicts the median tumor volume in a mouse model of human ovarian cancer (SKOV-3 cell line) with BI 853520 and PLD alone or in combination, showing the antitumor activity of different test groups. The test groups were group A (the control group); group B (the BI 853520 group administered once a day at a dose of 50 mg/kg); group C (the PLD group administered once a week at a dose of 5 mg/kg); and Group D (the combination group of BI 853520 and PLD, wherein BI 853520 was administered once a day at a dose of 50 mg/kg, and PLD was administered once a week at a dose of 5 mg/kg); respectively.

SKOV-3:

Group A had gained 0.3% body weight (Table 5), and the tumors had reached a median volume of 608 mm$^3$ on day 22 of treatment (FIG. 1b; Table 4).

Group B had a TGI of 57% (p=0.0136) with no tumor regression (FIG. 1b; Table 1). Animal body weight increased by 5.5% (p=0.9977 vs. group A) (Table 2).

Group C had a TGI of 66% (p=0.0136) with no tumor regression (FIG. 1b; Table 1). Animal body weight increased by 1.5% (p=0.6302 vs. Group A) (Table 2).

Group D had a TGI of 90% (p=0.0003 vs. group A; p=0.0070 vs. groups B and C), with tumor regression in 1 of 7 animals (FIG. 1b; Table 1). Animal body weight decreased by 1.4% (p=0.1349 vs. group A; p=0.0006 vs. group B; p=0.1588 vs. group C) (Table 2).

Studies have shown that the SKOV-3 cell line was less sensitive to both BI 853520 and PLD, and required higher drug doses (50 mg/kg, 5 mg/kg). Combination therapy was significantly more effective than monotherapy and the tolerance was not bad.

Figure 1C:
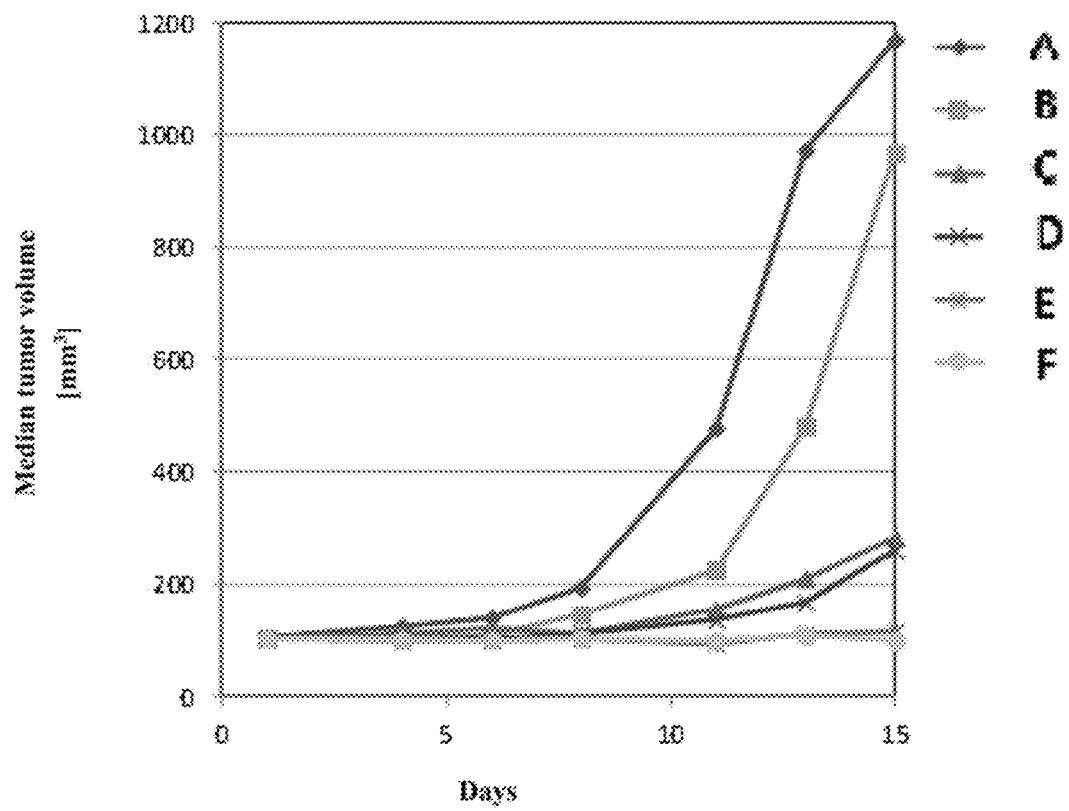
FIG. 1c depicts the median tumor volume in a mouse model of human ovarian cancer (A2780 cell line) with BI 853520 and PLD alone or in combination, showing the antitumor activity of different test groups. The test groups were group A (the control group); group B (the BI 853520 group administered once a day at a dose of 12.5 mg/kg); group C (the BI 853520 group administered once a day at a dose of 25 mg/kg); Group D (the BI 853520 group administered once a day at a dose of 50 mg/kg); Group E (the PLD group administered once a week at a dose of 5 mg/kg); and Group F (the combination group of BI 853520 and PLD, wherein BI 853520 was administered once a day at a dose of 50 mg/kg, and PLD was administered once a week at a dose of 5 mg/kg); respectively.

A2780:

Group A gained 12.5% body weight (FIG. 1c; Table 2), and the median tumor volume on day 15 of treatment was 1170 mm$^3$ (FIG. 1c; Table 1).

Group B had a TGI of 19% (p=0.1965) with no tumor regression (FIG. 1c; Table 1). Animal body weight increased by 10.6% (p=0.5251 vs. group A) (Table 2).

Group C had a TGI of 83% (p=0.0134) with no tumor regression (FIG. 1c; Table 1). Animal body weight increased by 12.6% (p=0.4789 vs. group A) (Table 2).

Group D had a TGI of 85% (p=0.0185) with no tumor regression (FIG. 1c; Table 1). Animal body weight increased by 10.1% (p=0.2280 vs. group A) (Table 2).

Group E had a TGI of 99% (p<0.0001), with tumor regression in 4 of 10 animals (FIG. 1c; Table 4). Animal body weight increased by 2.7% (p=0.0156 vs. group A) (Table 2).

Group F had a TGI of 100% (p<0.0001 vs. group A; p<0.0001 vs. group B; p=0.0376 vs. group C). Tumors regression occurred in 6 of 10 animals (FIG. 1c; Table 1). Animal body weight increased by 3.8% (p=0.0080 vs. group A; p=0.0021 vs. group B; p=0.5147 vs. group C) (Table 2).

Studies have shown that in the A2780 cell line, efficacy of BI 853520 was observed at medium and high dose levels (25 mg/kg, 50 mg/kg), but no tumor regression was found. High doses of PLD were highly potent, resulting in 40% tumor regression. Combination of BI 853520 and PLD resulted in higher efficacy with 60% regression while remaining well tolerated.

The combination of BI 853520 and PLD showed synergistic effects in ovarian cancer models of all three cell lines, with unaffected tolerance.

TABLE 1

Median tumor volume

| | Treatment | Dosage [mg/Kg] | Dosing interval | Median tumor volume [mm$^3$] | Tumor regression | TGI [%] |
|---|---|---|---|---|---|---|
| TOV-21G | A | — | qd | 654 | 0/10 | |
| | B | 12.5 | qd | 271 | 0/7 | 67 |
| | C | 1 | q7d | 178 | 0/7 | 83 |
| | D | 12.5 + 1 | qd + q7d | 47 | 6/7 | 106 |
| SKOV-3 | A | — | qd | 608 | 0/10 | |
| | B | 50 | qd | 306 | 0/7 | 57 |
| | C | 5 | q7d | 259 | 0/7 | 66 |
| | D | 50 + 5 | qd + q7d | 127 | 1/7 | 90 |
| A2780 | A | — | qd | 1170 | 0/10 | |
| | B | 12.5 | qd | 968 | 0/10 | 19 |
| | C | 25 | qd | 284 | 0/10 | 83 |
| | D | 50 | qd | 262 | 0/10 | 85 |
| | E | 5 | q7d | 117 | 4/10 | 99 |
| | F | 50 + 5 | qd + q7d | 100 | 6/10 | 100 |

TABLE 2

Change in median body weight at the end of the trial

| | Treatment | Dosage [mg/Kg] | Dosing interval | Change in median body weight [%] |
|---|---|---|---|---|
| TOV-21G | A | — | qd | -1.5 |
| | B | 12.5 | qd | +3.1 |
| | C | 1 | q7d | +1.6 |
| | D | 12.5 + 1 | qd + q7d | +1.4 |
| SKOV-3 | A | — | qd | +0.3 |
| | B | 50 | qd | +5.5 |
| | C | 5 | q7d | +1.5 |
| | D | 50 + 5 | qd + q7d | -1.4 |
| A2780 | A | — | qd | +12.5 |
| | B | 12.5 | qd | +10.6 |
| | C | 25 | qd | +12.6 |
| | D | 50 | qd | +10.1 |
| | E | 5 | q7d | +2.7 |
| | F | 50 + 5 | qd + q7d | +3.8 |

Example 2: Antitumor Activity Study of BI853520 in Combination with PLD in a ChampionsTumorGraft® PDX Ovarian Cancer Model The generic test method is as follows:

Female BomTac: approximately 7 weeks old (at start of dosing) NMRI-Foxn1nu mice were purchased from Taconic, Denmark. Body weights (at start of dosing) were approximately 20 grams. After arriving in the animal room, mice were acclimated to the new environment for at least 3 days. Immunocompromised female mice were housed in HEPA ventilated cages (Innocage® IVC, Innovive USA) at 68-74° F. (20-23° C.) and 30-70% humidity under a 12-hour light/12-hour dark cycle. Animals were provided with water (reverse osmosis, 2 ppm Cl$_2$) and a standard diet (Teklad 2919; 19% protein, 9% fat and 4% fiber) ad libitum. Animals with >10% body weight loss compared to day 0 received DietAel 76A (ClearH2O®, Portland, ME) for free. There were 3 mice in each group.

Mice were implanted with tumor cells from the ChampionsTumorGraft® ovarian model, which was established from patients previously treated with platinum-based therapy. After tumors reached 1000-1500 mm$^3$, they were collected, and tumor fragments SCs were implanted in the left flank of female pre-study mice. Each study animal was implanted with a specific passage batch. Tumor volume was measured twice a week with calipers to monitor tumor growth, and tumor volume (TV) was calculated using the formula (0.52×[length×width$^2$]). When TV reached approximately 250-350 mm$^3$ (average 300 mm$^3$), animals were matched to tumor size and assigned to the control or treatment groups (study mice) and dosing started on day 0. After initiation of dosing, animals were weighed daily using a digital scale and TV was measured twice weekly. The study was terminated when the mean tumor volume in the control group reached approximately 1500 mm$^3$ or until day 60. In some models, the study was extended beyond Day 60 and dosing was also extended to the end of the study. Individual animals could be removed from the study when tumor volume reaches approximately 1500 mm$^3$. The design of the antitumor effect study is shown in Table 3.

unknown (U) based on weight loss and by visual inspection. Mean % $vD_0$>20% and/or >10% mortality in the monotherapy or combination therapy groups were considered higher than the MTD of the treatment in the evaluated regimen. The maximum mean % $vD_0$ (body weight nadir) for each treatment group was reported at the end of the study.

Inhibitory effect on tumor growth was determined by calculating TGI (100%×[1−(final MTV−initial MTV of the treatment group)/(final MTV−initial MTV of the control group)]). Treatment was started on day 0. Tumor volumes in the treatment group were compared with those in the control group on the day the study was completed.

Other endpoints used to assess efficacy included number of CR, PR and TFS. PR and TFS were considered to exclude CR.

PR: TV≤30% of TV on day 0, in 2 consecutive measurements

CR: no TV could be detected (<4×4 mm$^2$), in 2 consecutive measurements

TFS: CR that persisted until the study was completed

Data were used for statistical analysis at the end of the study. Statistical comparisons of tumor volumes were performed using one-way analysis of variance followed by Newman-Keuls multiple comparison test to compare differences between all groups. Selected endpoints included as many groups as possible and as many animals per group as possible.

TABLE 3

Design of the antitumor effect study in a human ovarian cancer ChampionsTumorGraft®PDX model

| Group | n | Reagent | Dosage (mg/kg) | Volume dosage (mL/kg) | Route of administration | Dosing interval | Total dose |
|---|---|---|---|---|---|---|---|
| 1 | 3 | Control 1 |  | 10 | PO | BID | ≥120 |
|  |  | Control 2 |  | 5 | IV | q7d | ≥8 |
| 2 | 3 | BI 853520 | 50 | 5 | PO | BID | ≥120 |
| 3 | 3 | PLD | 3 | 10 | IV | q7d | ≥8 |
| 4 | 3 | BI 853520 | 50 | 10 | PO | BID | ≥120 |
|  |  | PLD | 3 | 5 | IV | q7d | ≥8 |
| 5 | 3 | Carboplatin | 25 | 10 | IP | q7d | 3 |
|  |  | Paclitaxel | 20 | 10 | IV | q7d | 3 |

Control 1: 0.5% Natrosol; control 2: 5% sterile glucose.

BI853520 was synthesized according to the method in the patent WO2010058032 and stored at room temperature in the dark.

The control group for oral administration was 0.5% Natrosol. The control group for intravenous administration was 5% sterile glucose.

Carboplatin was a pre-formulated 10 mg/mL stock solution. PLD was a pre-formulated 2 mg/mL stock solution. Paclitaxel was a pre-formulated 6 mg/mL stock solution. These standard chemotherapeutic drugs were provided by Champions.

To monitor side effects of the treatment, animals were observed daily from day 0 and weighed twice weekly. Data for each group, including body weight for each animal and mean body weight, were recorded, and the percentage change in mean body weight (% $vD_0$) for each group relative to Day 0 was recorded, and the % $vD_0$ was plotted at the completion of the study.

Animal deaths were recorded daily and determined as drug-related (D), technical (T), tumor-related (B), or unknown (U) based on weight loss and by visual inspection.

Tumor volumes from animals removed early due to tumor volume ≥1500 mm$^3$ were carried forward for analysis, but not more than 4 consecutive measurement time points. The tumor volumes of the combination group of BI 853520+ PLD, the BI 853520 group and the PLD group, and the sum of the tumor volumes of the BI 853520 group and the PLD group were compared.

Figure 2:
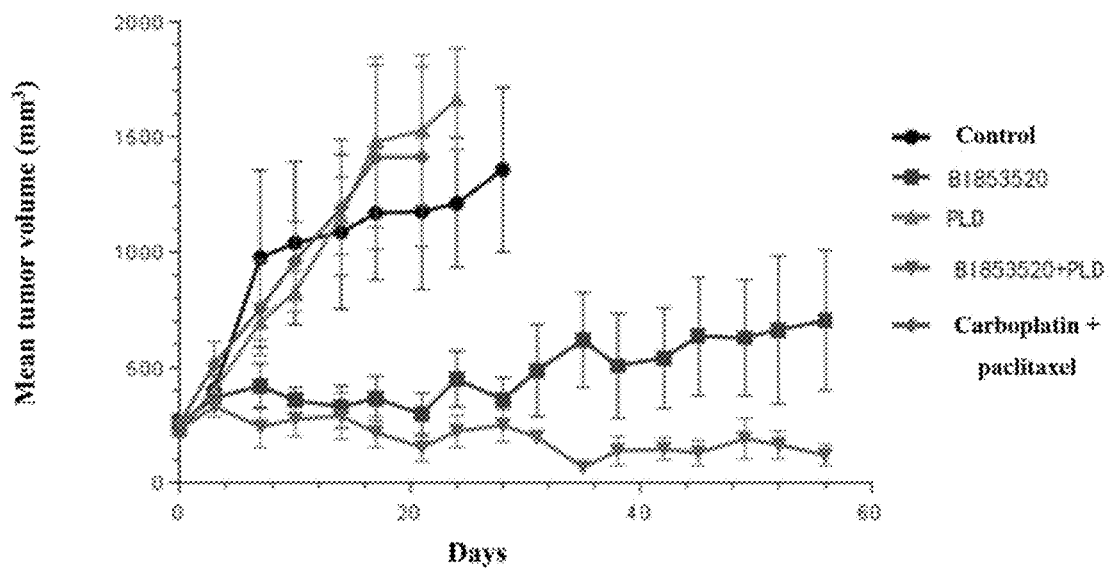
FIG. 2 depicts the tumor growth kinetics in a CTG-1166 model showing the antitumor activity of different test groups. The test groups were the control group; the BI 853520 group administered twice a day at a dose of 50 mg/kg; the PLD group administered once a week at a dose of 3 mg/kg; the combination group of BI 853520 and PLD, wherein BI 853520 was administered twice a day at a dose of 50 mg/kg, and PLD was administered once a week at a dose of 3 mg/kg; and the combination group of carboplatin and paclitaxel, wherein carboplatin was administered once a week for three weeks at a dose of 25 mg/kg, and paclitaxel was administered once a week for three weeks at a dose of 20 mg/kg; respectively.

Take the model CTG-1166 as an example:

The control group reached the endpoint on day 17. Treatment with PLD, and carboplatin/paclitaxel had no apparent antitumor activity (FIG. 2, Table 4). Continuing the experiment, it was shown that the BI 853520 group and the combination group of BI 853520 and PLD had a significant inhibitory effect on tumor growth (FIG. 2, Table 4). Meanwhile, the combination group of BI 853520 and PLD had 2 PRs (FIG. 2, Table 4). In the case of carboplatin and paclitaxel resistance, the combination group showed a good inhibitory effect. All groups were well tolerated, and no animals died (Table 5).

TABLE 4

Antitumor activity in a CTG-1166 model

| Group | Reagent | n | Dosage (mg/kg) | Dosing interval | Tumor volume (day 17) Mean ± SEM(mm³) | % TGI | Day 0-56 #PR/CR/TFS |
|---|---|---|---|---|---|---|---|
| 1 | Control | 3 | 0 | PO BID IV q7d | 1172 ± 289 | — | 0/0/0 |
| 2 | BI 853520 | 3 | 50 | PO BID | 366 ± 78 | 89 | 0/0/0 |
| 3 | PLD | 3 | 3 | IV q7d | 1479 ± 302 | −31 | 0/0/0 |
| 4 | BI 853520 PLD | 3 | 50 3 | PO BID IV q7d | 219 ± 55 | 101 | 2/0/0 |
| 5 | Carboplatin Paclitaxel | 3 | 25 20 | IP q7dx3 IV q7dx3 | 1411 ± 400 | −22 | 0/0/0 |

TABLE 5

Animal body weights in a CTG-1166 model

| Group | Reagent | n | Dosage (mg/kg) | Body weight (day 17) Mean ± SEM(g) | % vD$_0$ | Body weight nadir % vD$_{0(max)}$ | Day | Dead Total | Day |
|---|---|---|---|---|---|---|---|---|---|
| 1 | Control | 3 | 0, PO BID 0, IV q7d | 25.2 ± 0.2 | 5.5 | — | — | 0 | — |
| 2 | BI 853520 | 3 | 50, PO BID | 26.7 ± 0.4 | 4.0 | −0.7 | 13 | 0 | — |
| 3 | PLD | 3 | 3, IV q7d | 27.7 ± 1.4 | 9.2 | — | — | 0 | — |
| 4 | BI 853520 PLD | 3 | 50, PO BID 3, IV q7d | 25.9 ± 0.4 | 3.0 | — | — | 0 | — |
| 5 | Carboplatin Paclitaxel | 3 | 25, IP q7dx3 20, IV q7dx3 | 25.9 ± 1.0 | 5.4 | — | — | 0 | — |

Following the generic test method described above, the tumor inhibitory activity was also tested in CTG-0252, CTG-0257, CTG-0791, CTG-0868, CTG-0956, CTG-0958, CTG-0964, CTG-0992, CTG-1086, CTG-1180, CTG-1301, CTG-1395, CTG-1427, CTG-1433, CTG-1498, CTG-1602, CTG-1624, CTG-1627, CTG-1649, CTG-1677, CTG-1678, and CTG-1809, respectively. The results showed that in the above models, the combination group of BI 853520 and PLD had a significant synergistic effect and good antitumor activity (TGI>70%); for carboplatin and paclitaxel-resistant models (CTG-0791, CTG-0956, CTG-0964, CTG-0992, CTG-1180, CTG-1301, CTG-1433, CTG-1498 and CTG-1809), the combination group of BI 853520 and PLD still had good antitumor activity (TGI>70%) (Table 6).

TABLE 6

Antitumor activity in different ovarian cancer PDX models

| | | TGI (%) | | | |
|---|---|---|---|---|---|
| Model | Days | BI 853520 | PLD | BI 853520 + PLD | Carboplatin/ Paclitaxel |
| CTG-0252 | 7 | 54 | 39 | 80 | 59 |
| CTG-0257 | 30 | 67 | 54 | 87 | 106 |
| CTG-0791 | 35 | −21 | 52 | 74 | 5 |
| CTG-0868 | 25 | 54 | 36 | 73 | 74 |
| CTG-0956 | 67 | 77 | 56 | 97 | 20 |
| CTG-0958 | 52 | 99 | −17 | 113 | 89 |
| CTG-0964 | 35 | 66 | 47 | 79 | −9 |
| CTG-0992 | 60 | 49 | 57 | 101 | −2 |
| CTG-1086 | 28 | 39 | 62 | 86 | 56 |
| CTG-1180 | 42 | 33 | 4 | 82 | 23 |
| CTG-1301 | 38 | 43 | 70 | 81 | −24 |
| CTG-1395 | 33 | 41 | 39 | 91 | 102 |
| CTG-1427 | 42 | 59 | 57 | 98 | 115 |

TABLE 6-continued

Antitumor activity in different ovarian cancer PDX models

| | | TGI (%) | | | |
|---|---|---|---|---|---|
| Model | Days | BI 853520 | PLD | BI 853520 + PLD | Carboplatin/ Paclitaxel |
| CTG-1433 | 49 | 61 | 22 | 89 | −11 |
| CTG-1498 | 98 | 128 | 134(1PR) | 145(1PR) | 18 |
| CTG-1602 | 14 | −1 | 49 | 102 | 84 |
| CTG-1624 | 38 | 22 | 100 | 129 | 142 |
| CTG-1627 | 28 | 50 | 69 | 103 | 69 |
| CTG-1649 | 40 | 71 | 58 | 119(1 TFS) | 114 |
| CTG-1677 | 32 | 51 | 91 | 102 | 56 |
| CTG-1809 | 36 | −58 | 61 | 89 | −2 |

Days: Number of days until the end of the test
TGI > 70% (response); 30% < TGI < 70% (moderate); TGI < 30% (no response)

Studies have shown that in different PDX models, the combination of BI 853520 and PLD could produce higher efficacy, and it was still well tolerated. Especially for carboplatin and paclitaxel-resistant models, it still showed good antitumor activity.

Example 3: Study on the Antitumor Activity of BI853520 in Combination with Docetaxel in a PDX Gastric Cancer Model Female BomTac: NMRI-Foxn1nu mice were purchased from Taconic, Denmark. Mice were housed in individual ventilated cages (TECNIPLAST Sealsafe™-IVC-System, TECNIPLAST, Hohenpeissenberg, Germany), and type II or III cages were selected according to the number of experimental animals. The cages were under the conditions: 14L:10D light-dark cycle, air exchange (AC) rate of 60-65 AC/hr in the cage, 25±1° C. and 40-70% humidity. Animals were provided with water (sterilized tap water filtered and acidified (pH 2.5)) and animal diet (Teklad Global 19% protein squeeze diet (T.2019S.12)) ad libitum. Water and diet were changed twice a week, and all materials were autoclaved before use.

The GXA 3039 gastric cancer PDX model was used in this study. Tumor cells from the GXA 3039 gastric cancer PDX model were implanted into immunodeficient mice, and after primary implantation, tumor cells were established and characterized (passage 1). When tumor cells were passaged until a stable growth pattern was established, tumors were removed from mice and cut into segments (3-4 mm in edge length) and placed in PBS containing 10% penicillin/streptomycin. Tumor fragments were implanted subcutaneously into the flank of female pre-study mice. Tumor volume was measured daily with calipers to monitor tumor growth, and when TV reached 50-250 mm³ (preferably 80-200 mm³), they were randomized to the control or the treatment groups (so that the median and mean tumor volumes in each group were approximately 100-150 mm³). Animals that were not randomized were euthanized. The date of randomization was designated as day 0 of the test, and dosing began on day 1. After initiation of dosing, animals were observed and measured twice weekly for weight (daily if greater than 15% body weight loss was recorded) and absolute tumor volume (ATV). Animals were sacrificed ahead of schedule when the tumor ulcerated, or the tumor penetrated the skin, or the tumor volume was greater than 1500 mm³, or the weight loss was greater than 18%, or severe conditions such as numbness and pain occurred. If less than 70% of the original number of mice survived (i.e. less than 6 out of 8), the entire group was terminated. In order to be able to monitor tumor repopulation after the end of dosing, le Kaplan-Meier statistics were performed (this rule did not apply to the group in which the tumor had been remitted). Tolerability was assessed using the group with the largest median body weight loss (BWL) among groups.

Inhibition of tumor growth was determined by calculating TGI. TGI was calculated using the median absolute tumor volume (ATV) as follows:

$$ATV = a \times b^2 \times 0.5$$

where, a represents the length, and b represents the vertical tumor diameter;

$$TGI_x[\%] = \left(1 - \frac{T_x - T_0}{C_x - C_0}\right) \times 100$$

where $T_0$ and $C_0$ are the median ATVs of the test group and control group on day 0;

$T_x$ and $C_x$ are the corresponding median ATVs on Day X;
Day X is the day after the last dose of BI 853520 (administered QD), one week after the last dose of docetaxel (administered weekly), or the last day of at least 70% of the animals, whichever comes first.

TGI values have the following meanings (assuming $C_x > C_0$):
Overall tumor response in the test group: TGI>100%
Test tumor volume unchanged (stasis): TGI=100%
Reduced tumor growth rate compared to controls: 100%>TGI>0%
Same tumor growth rate compared to control group: TGI=0
Tumor growth stimulation compared to controls: TGI<0.

Additional endpoints used to assess efficacy included: time to tumor volume doubling/quadrupling and tumor growth delay/time to tumor progression/tumor repopulation.

Time to tumor volume doubling/quadrupling: The time to tumor volume doubling/quadrupling (Td/Tq) for the test and control groups was defined as the time interval (in days) required for each group to reach 200%/400% of the median RTV. The relative volume of a single tumor on day X ($RTV_x$ [%]) was obtained by dividing the absolute volume of the tumor on day X ($T_x$) by the absolute volume of the tumor on day 0 ($T_0$) and then multiplying it by 100, as follows:

$$RTV_x[\%] = \frac{T_x}{T_0} \times 100$$

Tumor growth delay/time to tumor progression/tumor repopulation: To assess the difference in time to tumor progression/tumor repopulation after tumor regression during the no-dose observation period (tumor growth delay, TGD), Kaplan-Meier survival analysis was used. A relative tumor volume of 400% was defined as the endpoint.

The design of the antitumor effect study is shown in Table 7.

TABLE 7

Design of antitumor effect study

| Group | n | Reagent | Dosage (mg/kg) | Route of administration | Dosing interval |
|---|---|---|---|---|---|
| 1 | 8 | Control 1 | 10 ml/kg | PO | qd |
|   |   | Control 2 | 10 ml/kg | IV | q7d |
| 2 | 8 | BI 853520 | 50 | PO | qd |
| 3 | 8 | Docetaxel | 10 | IV | q7d |
| 4 | 8 | BI 853520 + | 50 | PO | po |
|   |   | Docetaxel | 10 | IV | q7d |

Control 1: 0.5% Natrosol; Control 2: 0.9% saline.

BI853520 was synthesized according to the method in the patent WO2010058032 and stored at room temperature in the dark. BI 853520 was dissolved in 0.5% Natrosol to prepare a 5 mg/ml solution and administered at a dose of 50 mg/kg. The solution was divided into two equal parts, stored at room temperature in the dark, and used within one week.

Docetaxel was purchased from Sanofi Avents, and stored at 4° C. By diluting the docetaxel solution with 0.9% saline, a solution at a concentration of 1 mg/ml was prepared on the dosing day, and was administered at a dose of 10 mg/kg.

The control group for oral administration was 0.5% Natrosol. The control group for intravenous administration was 0.9% saline. Each dose was 10 ml/kg. For the combination group, docetaxel was administered immediately after BI 853520.

When significant weight loss was recorded in the test, the following measures will be taken:
for animals with more than 15% body weight loss, dosing was discontinued;
for animals with >15% body weight loss, body weight was measured daily;
for animals with more than 15% body weight loss, feed and water could conveniently be ingested;
dosing was resumed when individual animals reached at least 85% relative body weight.

Data were used for statistical analysis at the end of the study. The one-tailed nonparametric Mann-Whitney-Wilcoxon U test was used with the significance level a set at 0.05. The p-values obtained from the U-test were adjusted using the Bonferroni-Holm correction.

To assess the statistical significance of differences in time to tumor progression/tumor growth delay (TGD) using 400% of RTV as the trial endpoint, the Kaplan-Meier survival mode statistic was used in conjunction with the log-rank Mantel-Cox test for pairwise comparisons.

Additionally, to assess tolerance to treatment, a two-tailed nonparametric Mann-Whitney-Wilcoxon U test was performed using body weights determined at the end of the dosing period (i.e., on the day TGI values were calculated). In order not to overlook possible adverse effects of treatment, the Bonferroni-Holm method was not used to adjust the p-value for body weight, and weight loss was considered indicative if the p-value was within the range of $0.10 \geq p\text{-value} \geq 0.05$.

By convention, p-values≤0.05 represented significant tumor inhibition or weight loss. Statistical calculations were performed using GraphPad Prism® Bioanalysis software (version 6.01 for Windows®, GraphPad® Software, San Diego, CA, USA, graphpad.com).

Figure 3:
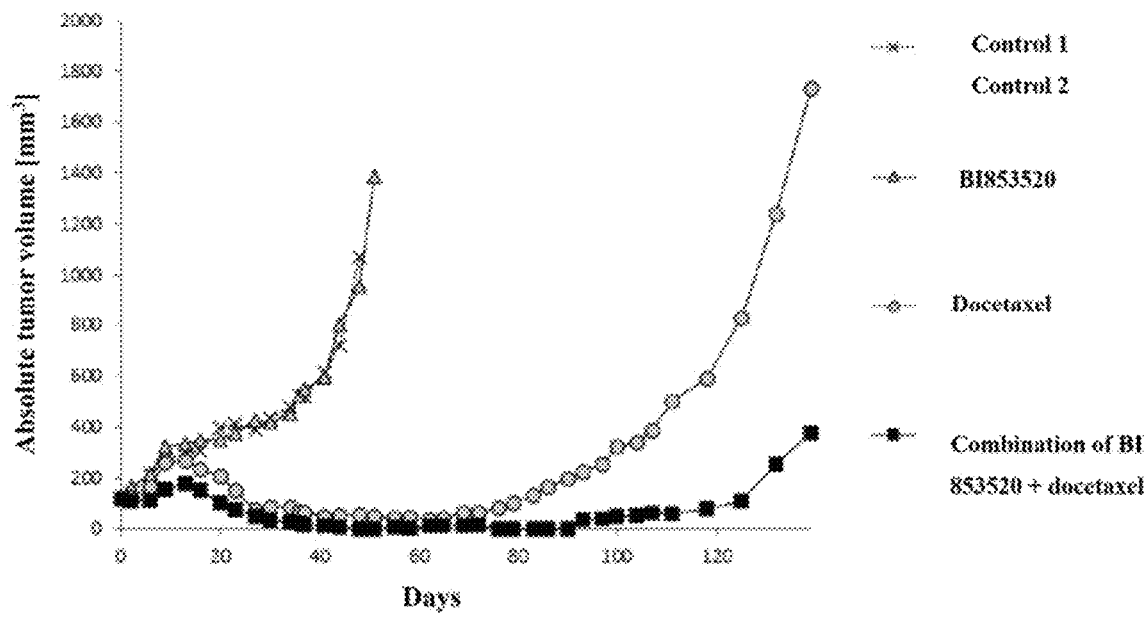
FIG. 3 depicts the tumor volume in a PDX model with B1853520 and docetaxel, showing the antitumor activity effect of different test groups. The test groups were the control group 1/the control group 2; the BI 853520 group administered once a day at a dose of 50 mg/kg; the docetaxel group administered once a week at a dose of 10 mg/kg; and the combination group of BI 853520 and docetaxel group, wherein BI 853520 was administered once a day at a dose of 50 mg/kg, and docetaxel was administered once a week at a dose of 10 mg/kg; respectively.

The study showed that the BI 853520 group had a TGI of 0%, which did not show any antitumor efficacy (Table 8, FIG. 3). The docetaxel group had a TGI of 113%, a data that was statistically significant compared to the control group (Table 8, FIG. 3). The combination group of BI 853520 and docetaxel had a TGI of 124%, a data that was statistically significant compared to the control group (Table 8, FIG. 3). In addition to showing better effect in tumor inhibition than the single drug groups, the combination group showed a more prominent advantage in the delay of tumor regrowth after the end of the administration. The Td was extended from about 7-8 days to 138 days, and the $T_q$ was not reached until the end of the test (Table 8, FIG. 3).

No or very few BWLs with a median maximum of 2.9% were observed in all groups. No median BWL was recorded in any of the BI 853520 groups (Table 9). Tolerance was good for all groups.

The combination of BI 853520 and docetaxel showed a synergistic effect in the GXA 3039 gastric cancer PDX model, and had a good inhibitory effect on tumor repopulation after drug withdrawal. Tolerance was not affected in the combination group.

Example 4: Efficacy of BI 853520 in a Mouse Model of Human Squamous Cell Lung Cancer (Cell Line NCI-H520)

Antitumor Research Methods with Generic Xenograft Models were adopted. Mice were approximately 6 weeks old. There were 5 mice in each group.

NCI-H520 cells were obtained from ATCC (HTB-182). MCB and WCB were established according to BI RCV GmbH & Co KG standard. Cells were incubated in a T175 tissue culture flask in a medium: GlutaMAX+F175K supplemented with 10% heat-inactivated fetal bovine serum and 1.5 g/l sodium bicarbonate. Cells were incubated at 37° C. and 5% $CO_2$. The cell concentration of the culture was maintained between $8 \times 10^6$ to $12 \times 10^7$ cells/tissue culture flask.

NCI-H520 cells were suspended in ice-cold PBS+5% FCS, and 100 μl of the cell suspension containing $5 \times 10^6$ cells was injected subcutaneously into the right flank of nude mice (1 site per mouse). When tumors formed and reached a median volume of 50 mm³ (14 days after cell injection), mice were randomly assigned to treatment and control groups.

The pH of the BI853520 formulation was 3.

Cisplatin was dissolved in 0.9% saline.

There were 10 animals in the control group and 7 animals in each treatment group.

A: Control group: 0.5% Natrosol/0.9% saline
B: BI 853520: 50 mg/kg (once a day, administered by gavage needle)
C: Cisplatin: 5 mg/kg (intraperitoneal injection once a week)
D: Combination of B+C

TABLE 8

Antitumor (gastric cancer) activity

| Group | Reagent | Dosage [mg/kg/d] | Administration Period | Administration Route | TGI [%] (d) | Td [d] | Tq [d] | P-value U test | P-value Kaplan-Meler |
|---|---|---|---|---|---|---|---|---|---|
| 1 | Control group 1 | 10 | 1-35 | PO | | 7.2 | 19.2 | | |
|   | Control group 2 | 10 | 1, 8, 15, 22, 29 | IV | | | | | |
| 2 | BI 853520 | 50 | 1-35 | PO | 0(36) | 8.1 | 41.2 | ns | ns |
| 3 | Docetaxel | 10 | 1, 8, 15, 22, 29 | IV | 113(36) | 8.5 | 108.0 | s | ns |
| 4 | BI 853520 | 50 | 1-35 | PO | 124(36) | 138.6 | nr | s | s |
|   | Docetaxel | 10 | 1, 8, 15, 22, 29 | IV | | | | | |

TABLE 9

Weight loss and survival rates

| Group | Reagent | Dosage [mg/kg/d] | Administration Period | The last day | Median BWL maximum [%](d) | Survival rate |
|---|---|---|---|---|---|---|
| 1 | Control group 1 | 10 | 1-35 | 51 | 1.6(13) | 4/8 |
|   | Control group 2 | 10 | 1, 8, 15, 22, 29 | | | |
| 2 | BI 853520 | 50 | 1-35 | 51 | nr | 4/8 |
| 3 | Docetaxel | 10 | 1, 8, 15, 22, 29 | 140 | 2.1(2) | 2/8 |
| 4 | BI 853520 | 50 | 1-35 | 140 | 2.9(16) | 6/8 |
|   | Docetaxel | 10 | 1, 8, 15, 22, 29 | | | | nr represented not reached, no weight loss (e.g. median RBW of a group was always greater than 100%).

Tumor volume was statistically evaluated at the end of the test on day 22. Statistical evaluation was performed using the Student's t-test function in Microsoft Excel, utilizing a two-tailed distribution and a two-sample equal variance type.

Animals in group A gained 5.8% body weight (Table 10), and the tumors had reached a median volume of 721 mm$^3$ by day 22 of treatment (Table 10).

Figure 4:
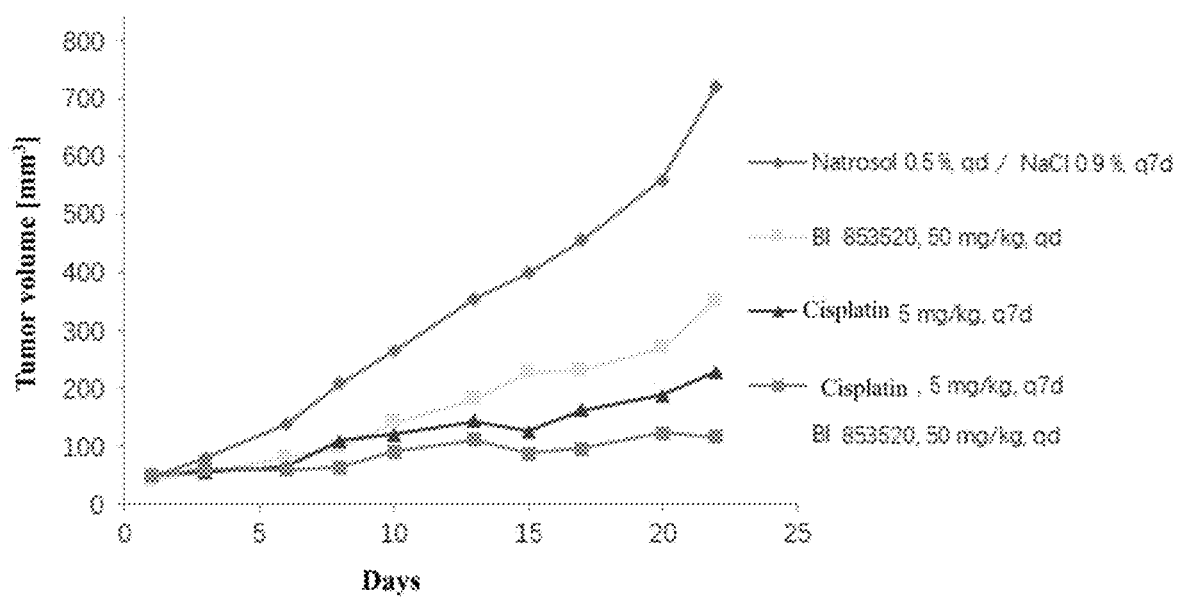
FIG. 4 depicts the tumor volume (mm$^3$) in a nude mouse xenograft model of human squamous cell lung cancer (cell line NCI-H520) showing the antitumor effects of different test groups. The test groups were the control group; the BI 853520 group administered once a day at a dose of 50 mg/kg; the cisplatin group administered once a week at a dose of 5 mg/kg; and the combination group of BI 853520 and cisplatin, wherein BI 853520 was administered once a day at a dose of 50 mg/kg, and cisplatin was administered once a week at a dose of 5 mg/kg; respectively.

Group B had a TGI of 54% (p=0.007) (FIG. 4, Table 10). The median animal body weight increased by 9.1% (Table 10).

Group C significantly inhibited tumor growth with a TGI of 74% (p=0.0004, Table 10, FIG. 4). Treatment was well tolerated, with the median body weight increased by 9.6% (Table 10).

Group D had a TGI of 90% (p=0.00003) and tumor regression in 2/7 (Table 10, FIG. 4). Treated animals showed minimal body weight change (−0.1%) (Table 10).

The study showed that BI 853520 showed statistically significant tumor inhibitory activity (p<0.05) at 50 mg/kg, and was well tolerated. In addition, when BI 853520 was used in combination with cisplatin (5 mg/kg, IP, q7d), better tumor inhibitory activity was observed with good tolerance and no significant weight loss.

BI 853520 was potent in the NCI-H520 human squamous cell lung cancer xenograft model, and its combination with cisplatin showed better antitumor effect than either single drug.

TABLE 10

| Treatment | Median tumor volume [mm$^3$] | Median TGI [%] | Tumor regression | Change in median body weight [%] |
|---|---|---|---|---|
| A | 721 | | 0/10 | +5.8 |
| B | 352 | 54 | 0/7 | +9.1 |
| C | 228 | 74 | 0/7 | +9.6 |
| D | 116 | 90 | 2/7 | −0.1 |

Example 5: Antitumor Activity Study of BI 853520 in Combination with Paclitaxel in a Mouse Model (Cell Line KYSE-270)

Antitumor Research Methods with Generic Xenograft Models were adopted. Mice were approximately 8-10 weeks old. There were 7-10 mice in each group.

KYSE-270 was a cell line for esophageal cancer (Public Health England, Cat. No. 94072021). Cells were incubated in a T175 tissue culture flask in a medium: RPMI-1640+ HAMF2 (1:1) supplemented with 2% calf serum and 2 nM glutamine. Cells were incubated at 37° C. and 5% $CO_2$.

KYSE-270 cells were suspended in PBS+5% FCS at a cell inoculation level of 5×10$^6$ cells/ml. When tumors formed and reached 94-252 mm$^3$ (13 days after cell injection), mice were randomly assigned to treatment and control groups.

There were 10 animals in the control group and 7 animals in each treatment group.
  A: Control group: 0.5% Natrosol/0.9 NaCl
  B: BI 853520: 50 mg/kg (once a day, administered by gavage needle)
  C: Paclitaxel: 10 mg/kg (once a week, administered by intravenous bolus)
  D: Combination of B+C At the end of the trial, comparisons were made by the exact Wilcoxon test.

Figure 5:
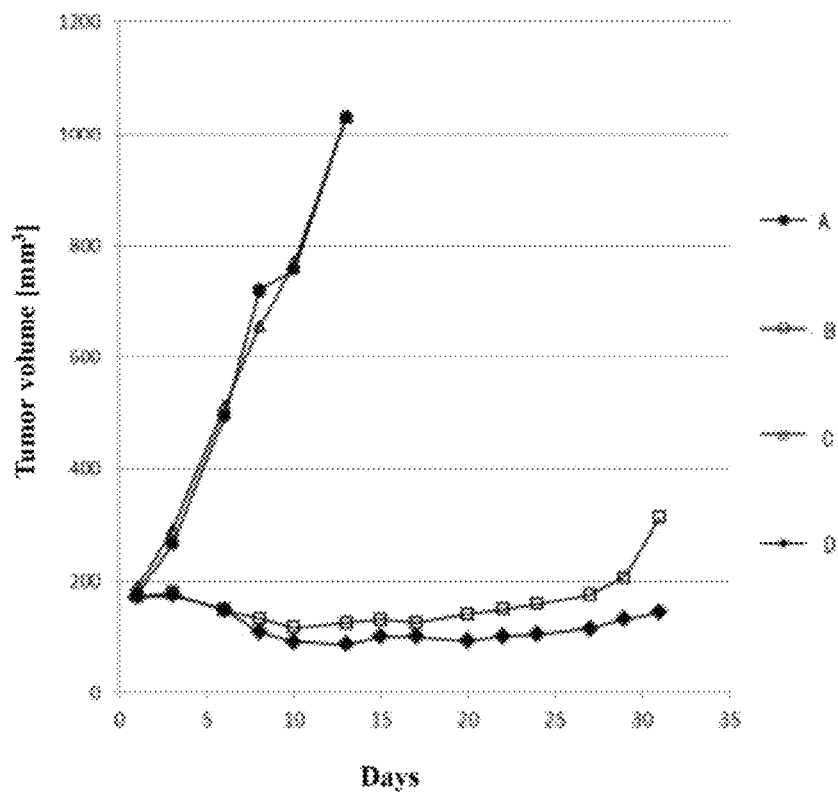
FIG. 5 depicts the tumor volume (mm$^3$) in a nude mouse xenograft model of human esophageal cancer (cell line KYSE-270) showing the antitumor effects of different test groups. The test groups were the control groups; the BI 853520 group administered once a day at a dose of 50 mg/kg; the paclitaxel group administered once a week at a dose of 10 mg/kg; the combination group of BI 853520 and paclitaxel, wherein BI 853520 was administered once a day at a dose of 50 mg/kg, and paclitaxel was administered once a week at a dose of 10 mg/kg; respectively.

In group A, the tumors had reached a median volume of 1032 mm$^3$ by day 13 of treatment (FIG. 5; Table 11). Animals lost 9.1% body weight (Table 11) and one animal had to be euthanized ahead of schedule due to severe weight loss on day 9.

Tumor growth was significantly delayed in group B compared to the control group, with a TGI of 106% (p=0.0003) (FIG. 5; Table 11). Tumor regression had occurred in 6 of 7 animals, and all survived. Animal body weight increased by 2.8% (p=0.9999 vs. group A) (Table 11).

There was no effect on tumor growth in group C compared to the control group, with a TGI of 2% (p=0.3788), and no tumor regression (FIG. 5; Table 11). Animal body weight decreased by 9.7% (p=0.7320 vs. group A) (Table 11).

Tumor growth was significantly delayed in group D compared to the control group, with a TGI of 110% (p=0.0003 vs. Group A) and tumor regression had occurred in 7 of 7 animals (FIG. 5; Table 11). Animal body weight increased by 3.5% (p=1.0000 vs. Group A) (Table 11).

Studies have shown that in the subcutaneous human KYSE-270 esophageal cancer model, 50 mg/kg BI 853520 as a single drug had inhibitory effect on tumor growth, but 10 mg/kg paclitaxel as a single drug had no effect. In contrast, the combination of the two drugs had better inhibitory effect, and tumor regression had occurred in 7 of the 7 animals with good tolerance. Especially after drug withdrawal, the tumor size did not increase significantly.

TABLE 11

| Treatment | Dosage [mg/Kg] | Dosing interval | Median tumor volume [mm$^3$] | Tumor regression | TGI [%] | Change in median body weight [%] |
|---|---|---|---|---|---|---|
| A | — | qd/q7d | 1032 | | | −10.3 |
| B | 50 | qd | 126 | 6/7 | 106 | 2.8 |
| C | 10 | q7d | 1033 | 0/7 | 2 | −9.7 |
| D | 50 + 10 | qd + q7d | 87 | 7/7 | 110 | 3.5 |

Example 6: Antitumor Activity Study of BI 853520 in Combination with Docetaxel in a Mouse Model (Cell Lines KYSE-70, PC-3 and HS 746T)

Antitumor Research Methods with Generic Xenograft Models were adopted.

KYSE-70: Approximately 8-10 week old mice. There were 7-10 mice in each group.

PC-3: Approximately 6 week old mice. There were 7-10 mice in each group.

HS 746T: Approximately 6 week old mice. There were 7-10 mice in each group.

KYSE-70 was a cell line for esophageal cancer (HPA strain deposit, Cat. No. 94072012). Both PC-3 and HS 746T were purchased from ATCC. Cells were incubated in a T175 tissue culture flask in a medium: RPMI-1640 supplemented with 10% calf serum. Cells were incubated at 37° C. and 5% $CO_2$.

KYSE-70 cells were suspended in PBS+5% FCS at a cell inoculation level of $5×10^6$ cells/(50 uL culture medium+50 uL Matrigel). When tumors formed and reached 67-93 $mm^3$ (11 days after cell injection), mice were randomly assigned to treatment and control groups.

PC-3 cells were suspended in PBS+5% FCS at a cell inoculation level of $5×10^6$ cells/(50 uL culture medium+50 uL Matrigel). When tumors formed and reached 100 $mm^3$ (11 days after cell injection), mice were randomly assigned to treatment and control groups.

HS 746T cells were suspended in PBS+5% FCS at a cell inoculation level of $1×10^7$ cells/(50 uL culture medium+50 uL Matrigel). When tumors formed and reached 117 $mm^3$ (10 days after cell injection), mice were randomly assigned to treatment and control groups.

KYSE-70 and HS 746T:

There were 10 animals in the control group and 7 animals in each treatment group.

A: Control group: 0.5% Natrosol/5 glucose

B: BI 853520: 50 mg/kg (once a day, administered by gavage needle)

C: Docetaxel: 10 mg/kg (once a week, administered by intravenous bolus)

D: Combination of B+C

PC-3:

There were 10 animals in the control group and 7 animals in each treatment group.

A: Control group: 0.5% Natrosol/5 glucose

B: BI 853520: 25 mg/kg (once a day, administered by gavage needle)

C: Docetaxel: 7.5 mg/kg (once a week, administered by intravenous bolus)

D: Combination of B+C

At the end of the trial, comparisons were made by the exact Wilcoxon test.

Figure 6:
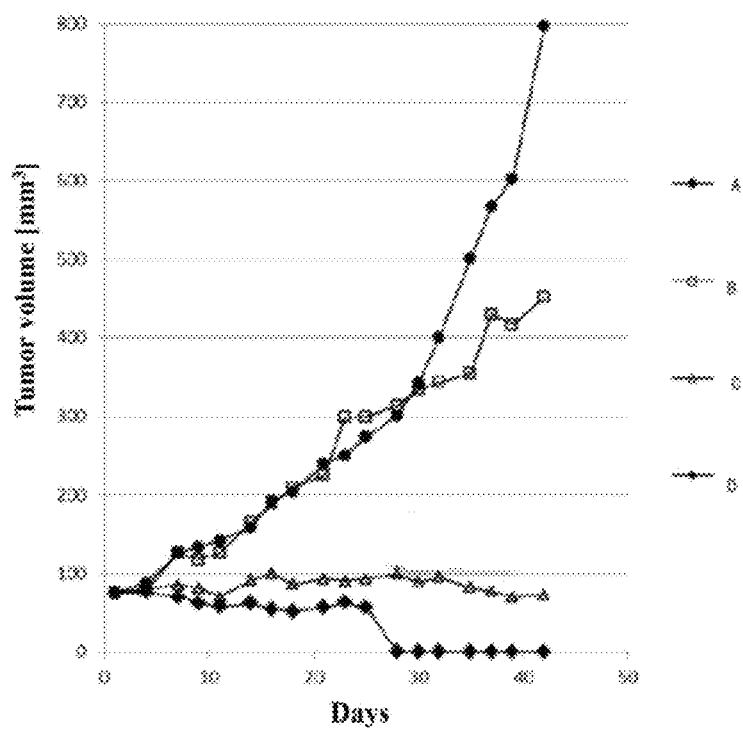
FIG. 6 depicts the tumor volume (mm$^3$) in a nude mouse xenograft model of human esophageal cancer (cell line KYSE-70) showing the antitumor effects of different test groups. The test groups were the control group; the BI 853520 group administered once a day at a dose of 50 mg/kg; the docetaxel group administered once a week at a dose of 10 mg/kg; and the combination group of BI 853520 and docetaxel, wherein BI 853520 was administered once a day at a dose of 50 mg/kg, and docetaxel was administered once a week at a dose of 10 mg/kg; respectively.

KYSE-70:

In group A, the tumors had grown from a median volume of 76 $mm^3$ to a median volume of 798 $mm^3$ by day 42 (FIG. 6; Table 12). Animal body weight increased by 7.0% (Table 12).

Tumor growth was not significantly delayed in group B compared to the control group, with a TGI of 42% (p=0.1574) (FIG. 6; Table 12). Tumor regression had occurred in 1 of the 7 animals. Animal body weight increased by 8.8% (p=0.7189 vs. group A) (Table 12).

Tumor growth was significantly delayed in group C compared to the control group, with a TGI of 100% (p=0.0002), and tumor regression had occurred in 4 of 7 animals by day 28 (FIG. 6; Table 12). Animal body weight increased by 5.6% (p=0.2681 vs. group A) (Table 12).

Tumor growth was significantly delayed in group D compared to the control group, with a TGI of 111% (p=0.0002 vs. group A) and tumor regression had occurred in 7 of 7 animals (FIG. 6; Table 11). Animal body weight increased by 2.5% (p=0.0093 vs. group A) (Table 12).

Studies have shown that in the subcutaneous human KYSE-70 esophageal cancer model, 50 mg/kg BI 853520 as a single drug had no inhibitory effect on tumor growth, but 10 mg/kg docetaxel as a single drug had inhibitory effect. In contrast, the combination of the two drugs had a better inhibitory effect (tumor regression occurred in 6 of the 7 animals, and the median tumor volume reached 0 with good tolerance).

PC-3: (Withdrawal on Day 28)

Figure 7:
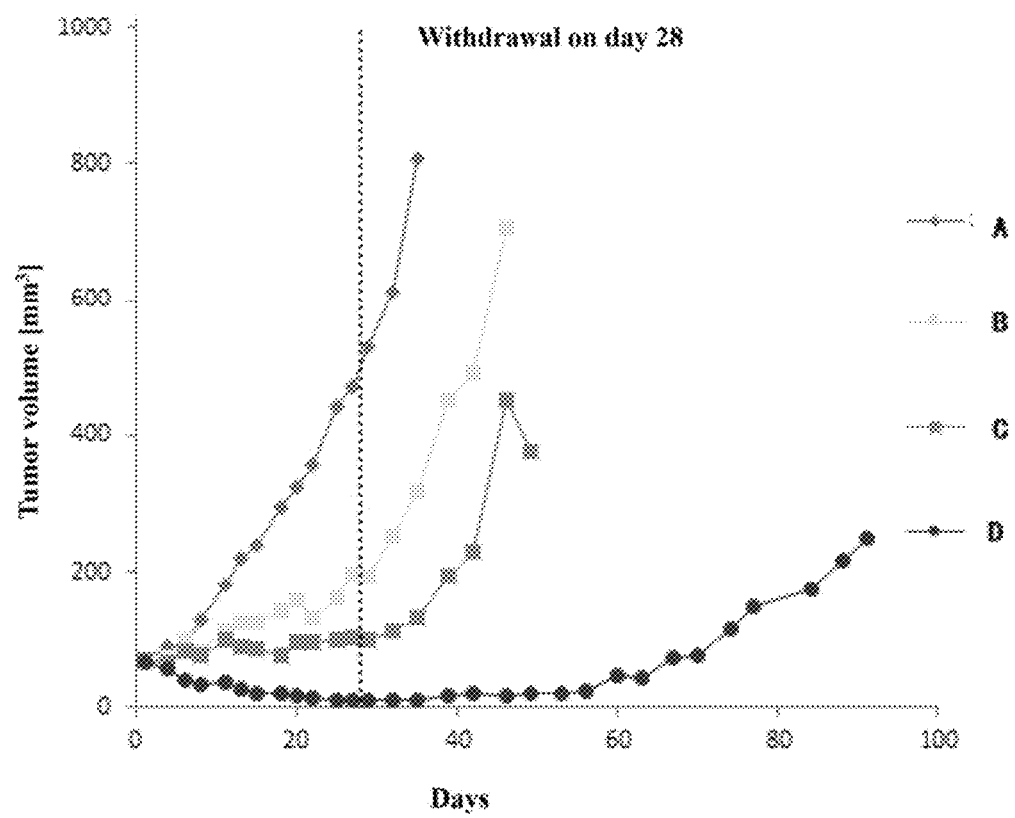
FIG. 7 depicts the tumor volume (mm$^3$) in a nude mouse xenograft model of human prostate cancer (cell line PC-3) showing the antitumor effect of different test groups. The test groups were the control groups; the BI 853520 group administered once a day at a dose of 25 mg/kg; the docetaxel group administered once a week at a dose of 7.5 mg/kg; and the combination group of BI 853520 and docetaxel, wherein BI 853520 was administered once a day at a dose of 25 mg/kg, and docetaxel was administered once a week at a dose of 7.5 mg/kg; respectively.

In group A, the tumors had grown from a median volume of 70 $mm^3$ to a median volume of 809 $mm^3$ by day 35 (FIG. 7; Table 12). Animal body weight decreased by 3.2% (Table 12).

Tumor growth was significantly delayed in group B compared to the control group with a TGI of 66% (FIG. 7; Table 12). Animal body weight increased by 2.4% (Table 12).

Tumor growth was significantly delayed in group C compared to the control group, with a TGI of 92%, and tumor regression had occurred in 3 of 7 animals by day 28 (FIG. 7; Table 12). Animal body weight increased by 10% (Table 12).

Tumor growth was significantly delayed in group D compared to the control group with a TGI of 108%, and tumor regression had occurred in 6 of 7 animals (FIG. 7; Table 12). Animal body weight increased by 7.8% (Table 12).

Studies have shown that in the subcutaneous human PC-3 prostate cancer model, 25 mg/kg BI 853520 as a single drug and 7.5 mg/kg docetaxel as a single drug had a certain inhibitory effect on tumor growth. The combination of the two drugs had obvious synergistic effect, with tumor regression occurred in 6 of 7 animals, and tumor growth was still inhibited after drug withdrawal. The tolerance was good.

HS 746T: (Withdrawal on Day 28)

Figure 8:
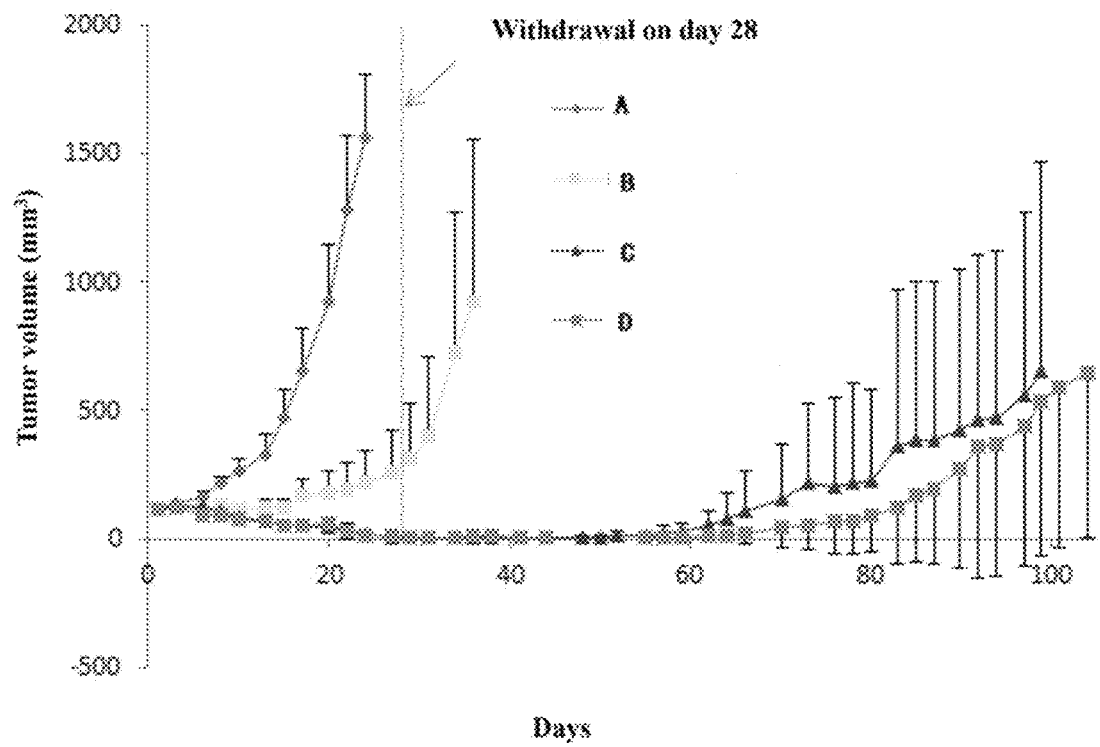
FIG. 8 depicts the tumor volume (mm$^3$) in a nude mouse xenograft model of human gastric cancer (cell line HS 746T) showing the antitumor effects of different test groups. The test groups were the control group; the BI 853520 group administered once a day at a dose of 50 mg/kg; the docetaxel group administered once a week at a dose of 10 mg/kg; and the combination group of BI 853520 and docetaxel, wherein BI 853520 was administered once a day at a dose of 50 mg/kg once a day and docetaxel was administered once a week at a dose of 10 mg/kg; respectively.

In group A, the tumors had grown from a median volume of 117 $mm^3$ to a median volume of 1684 $mm^3$ by day 24 (FIG. 8; Table 12). Animal body weight increased by 8.4% (Table 12).

Tumor growth was significantly delayed in group B compared to the control group with a TGI of 93% (FIG. 8; Table 12). Tumor regression had occurred in 1 of 8 animals. Animal body weight increased by 7.3% (Table 12).

Tumor growth was significantly delayed in group C compared to the control group, with a TGI of 108%, and tumor regression had occurred in all 8 animals by day 28 (FIG. 8; Table 12). Animal body weight increased by 6.7% (Table 12).

Tumor growth was significantly delayed in group D compared to the control group with a TGI of 108%, and tumor regression had occurred in all 8 animals (FIG. 8; Table 12). Animal body weight increased by 9.3% (Table 12).

Studies have shown that in subcutaneous human HS 746T gastric cancer model, 50 mg/kg BI 853520 as a single drug or 10 mg/kg docetaxel as a single drug had inhibitory effect. In contrast, the combination of the two drugs had better inhibitory effect (All of the 8 animals showed tumor regression, and the tumor growth was still inhibited after drug withdrawal. There was a longer-lasting antitumor effect especially in the combination group, and the tolerance was good).

TABLE 12

| | | | | Median tumor volume | | | |
|---|---|---|---|---|---|---|---|
| Cell Line | Treatment | Dosage [mg/Kg] | Dosing interval | Median tumor volume [mm³] | Tumor regression | TGI [%] | Change in median body weight [%] |
| KYSE-70 | A | — | qd/q7d | 798 | | | 7.0 |
| | B | 50 | qd | 497 | 1/7 | 42 | 8.8 |
| | C | 10 | q7d | 73 | 4/7 | 100 | 5.6 |
| | D | 50 + 10 | qd + q7d | 0 | 6/7 | 111 | 2.5 |
| PC-3 | A | — | qd/q7d | 809 | 0/7 | | −3.2 |
| | B | 25 | qd | 316 | 0/7 | 66 | 2.4 |
| | C | 7.5 | q7d | 131 | 3/7 | 92 | 10 |
| | D | 25 + 7.5 | qd + q7d | 9.95 | 6/7 | 108 | 7.8 |
| HS 746T | A | — | qd/q7d | 1684 | 0/10 | | 8.4 |
| | B | 50 | qd | 229 | 1/8 | 93 | 7.3 |
| | C | 10 | q7d | 0 | 8/8 | 108 | 6.7 |
| | D | 50 + 10 | qd + q7d | 0 | 8/8 | 108 | 9.3 |

The contents of all references (including literature references, issued patents, published patent applications, and co-pending patent applications) cited throughout this application are expressly incorporated herein by reference in their entirety. Unless otherwise defined, all technical and scientific terms used herein have the same meaning as commonly known to those skilled in the art.

All features disclosed in this specification may be combined in any combination. Each feature disclosed in this specification may be replaced by alternative features serving the same, equivalent or similar purpose. Thus, unless expressly stated otherwise, each feature disclosed is only an example of a series of equivalent or similar features.

From the above description, one skilled in the art can easily ascertain the essential characteristics of this invention, and can make various changes and modifications of the invention without departing from the spirit and scope of the invention to adapt them to various usages and conditions. Accordingly, other embodiments are within the scope of the appended claims.

What is claimed is:

1. A pharmaceutical combination comprising:
BI853520 or a pharmaceutically acceptable salt thereof, and
a chemotherapeutic drug which is PLD, docetaxel, or paclitaxel;
wherein the BI853520 has a structural formula of:

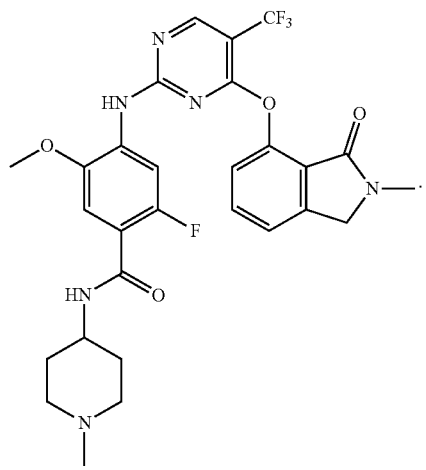

2. The pharmaceutical combination of claim 1, wherein the chemotherapeutic drug is PLD.

3. The pharmaceutical combination of claim 1, wherein the chemotherapeutic drug is docetaxel, or paclitaxel.

4. The pharmaceutical combination of claim 1, wherein the pharmaceutically acceptable salt is BI853520 tartrate.

5. A method for treating a tumor in a subject, which comprises administering to the subject i) an effective amount of BI853520 or a pharmaceutically acceptable salt thereof and ii) an effective amount of a chemotherapeutic drug which is PLD, docetaxel, or paclitaxel; wherein the BI853520 has a structural formula of:

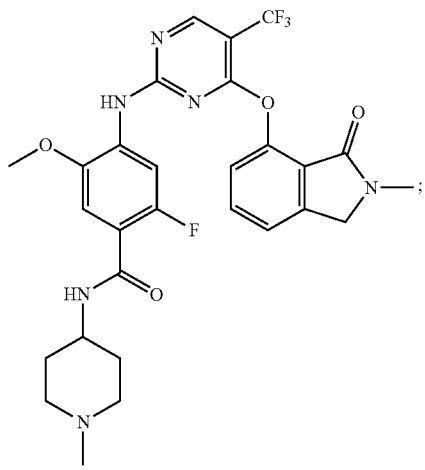

and
wherein the tumor is ovarian cancer, gastric cancer, prostate cancer, esophageal cancer, or lung cancer.

6. The method of claim 5, wherein the chemotherapeutic drug is PLD.

7. The method of claim 6, wherein the tumor is ovarian cancer.

8. The method of claim 5, wherein the chemotherapeutic drug is docetaxel, or paclitaxel.

9. The method of claim 8, wherein the tumor is prostate cancer, esophageal cancer or gastric cancer.

10. The method of claim 5, wherein the BI853520 or a pharmaceutically acceptable salt thereof and the chemotherapeutic drug are administered simultaneously, alternately or sequentially.

11. The method of claim 5, wherein the pharmaceutically acceptable salt is BI853520 tartrate.

12. The method of claim 7, wherein the tumor is platinum-resistant ovarian cancer.

13. The method of claim 5, wherein the chemotherapeutic drug is docetaxel.

14. The method of claim 5, wherein the chemotherapeutic drug is paclitaxel.

15. The method of claim 5, wherein the tumor is prostate cancer.

16. The method of claim 5, wherein the tumor is esophageal cancer.

17. The method of claim 5, wherein the tumor is gastric cancer.

* * * * *